(12) United States Patent
Bushman et al.

(10) Patent No.: US 8,256,464 B2
(45) Date of Patent: Sep. 4, 2012

(54) CHECK VALVE FLAP FOR FLUID INJECTOR

(75) Inventors: Richard Paul Bushman, Stillwater, MN (US); Jerry Schueller, Bloomington, MN (US)

(73) Assignee: RJC Products LLC, Lake Elmo, MN (US)

( * ) Notice: Subject to any disclaimer, the term of this patent is extended or adjusted under 35 U.S.C. 154(b) by 406 days.

(21) Appl. No.: 12/163,377

(22) Filed: Jun. 27, 2008

(65) Prior Publication Data

US 2009/0065067 A1    Mar. 12, 2009

Related U.S. Application Data

(63) Continuation of application No. 11/751,803, filed on May 22, 2007, and a continuation of application No. PCT/US2008/064302, filed on May 21, 2008.

(51) Int. Cl.
*F16K 15/14* (2006.01)
(52) U.S. Cl. .................................. 137/852; 137/855
(58) Field of Classification Search ............... 137/856, 137/855, 852, 843, 527, 515.5; 251/331
See application file for complete search history.

(56) References Cited

U.S. PATENT DOCUMENTS

| | | | |
|---|---|---|---|
| 2,378,613 A | 6/1945 | Young et al. | |
| 2,707,965 A | 5/1955 | Allen | |
| 2,864,394 A * | 12/1958 | Hempel | 137/517 |
| 2,867,213 A | 1/1959 | Thomas, Jr. | |
| 3,292,658 A | 12/1966 | Scaramucci | |
| 3,417,750 A | 12/1968 | Carson | |
| 3,463,159 A | 8/1969 | Heimlich | |
| 3,570,525 A | 3/1971 | Borsum et al. | |
| 3,572,375 A | 3/1971 | Rosenberg | |
| 3,626,980 A | 12/1971 | Svensson | |
| 3,628,565 A * | 12/1971 | McWethy et al. | 137/855 |
| 3,807,444 A | 4/1974 | Fortune | |
| 3,910,283 A * | 10/1975 | Leveen | 604/9 |
| 4,009,366 A | 2/1977 | Danell | |
| 4,081,176 A | 3/1978 | Johnson | |
| 4,083,115 A | 4/1978 | McKelvey | |
| 4,160,383 A | 7/1979 | Rauschenberger | |
| 4,232,677 A | 11/1980 | Leibinsohn | |
| 4,286,622 A | 9/1981 | Ninomiya et al. | |
| 4,405,316 A | 9/1983 | Mittleman | |
| 4,474,209 A | 10/1984 | Akhtarekhavari | |

(Continued)

FOREIGN PATENT DOCUMENTS

EP    0 546 233 A    6/1993

OTHER PUBLICATIONS

International Search Report dated Jan. 29, 2010 for International Application No. PCT/US2009/048692 (3 pages).

(Continued)

*Primary Examiner* — Kevin Lee
*Assistant Examiner* — Macade Brown
(74) *Attorney, Agent, or Firm* — Holland & Hart LLP

(57) ABSTRACT

A backflow-prevention system that substantially prevents contaminant backflow at a treatment site. The system includes a fluid ejector tube for insertion into the patient's mouth and a backflow prevention device that receives fluid from the fluid ejector tube. The backflow prevention device includes an internally positioned valve member. The valve member limits contaminant backflow. The valve member is movable between open and closed positions based on a vacuum pressure condition in the system.

26 Claims, 27 Drawing Sheets

U.S. PATENT DOCUMENTS

| | | |
|---|---|---|
| 4,538,508 A | 9/1985 | Ballard |
| 4,556,086 A | 12/1985 | Raines |
| 4,610,275 A * | 9/1986 | Beecher ............... 137/854 |
| 4,610,276 A | 9/1986 | Paradis et al. |
| 4,683,916 A | 8/1987 | Raines |
| 4,723,912 A | 2/1988 | Nieusma |
| 4,735,607 A | 4/1988 | Keith, Jr. |
| 4,758,224 A | 7/1988 | Siposs |
| 4,810,194 A | 3/1989 | Snedden |
| 4,904,236 A | 2/1990 | Redmond et al. |
| 4,966,551 A | 10/1990 | Betush |
| 4,998,880 A | 3/1991 | Nerli |
| 5,044,953 A | 9/1991 | Sullivan |
| 5,114,342 A | 5/1992 | Young et al. |
| 5,158,539 A | 10/1992 | Kolff et al. |
| 5,165,891 A | 11/1992 | Young et al. |
| 5,176,658 A | 1/1993 | Ranford |
| 5,242,398 A | 9/1993 | Knoll et al. |
| 5,267,586 A | 12/1993 | Jankavaara |
| 5,295,478 A * | 3/1994 | Baldwin ............. 128/203.11 |
| 5,295,830 A | 3/1994 | Shen et al. |
| 5,413,142 A | 5/1995 | Johnson et al. |
| 5,425,637 A | 6/1995 | Whitehouse et al. |
| 5,441,410 A | 8/1995 | Segerdal |
| 5,453,097 A | 9/1995 | Paradis |
| 5,464,350 A | 11/1995 | Bierbaum |
| 5,464,397 A | 11/1995 | Powers, Jr. |
| 5,509,802 A | 4/1996 | Whitehouse et al. |
| 5,520,041 A | 5/1996 | Hasell |
| 5,535,785 A | 7/1996 | Werge et al. |
| 5,725,374 A | 3/1998 | Young |
| 5,855,478 A | 1/1999 | Van |
| 5,921,776 A | 7/1999 | Heilbrunn |
| 5,992,462 A | 11/1999 | Atkinson et al. |
| 6,089,272 A * | 7/2000 | Brand et al. ............... 137/859 |
| 6,203,321 B1 | 3/2001 | Helmer et al. |
| 7,131,839 B2 | 11/2006 | March |
| 2005/0085746 A1 | 4/2005 | Adams et al. |

OTHER PUBLICATIONS

International Search Report dated Nov. 14, 2008 for International Application No. PCT/US2008/064302 (6 pages).

* cited by examiner

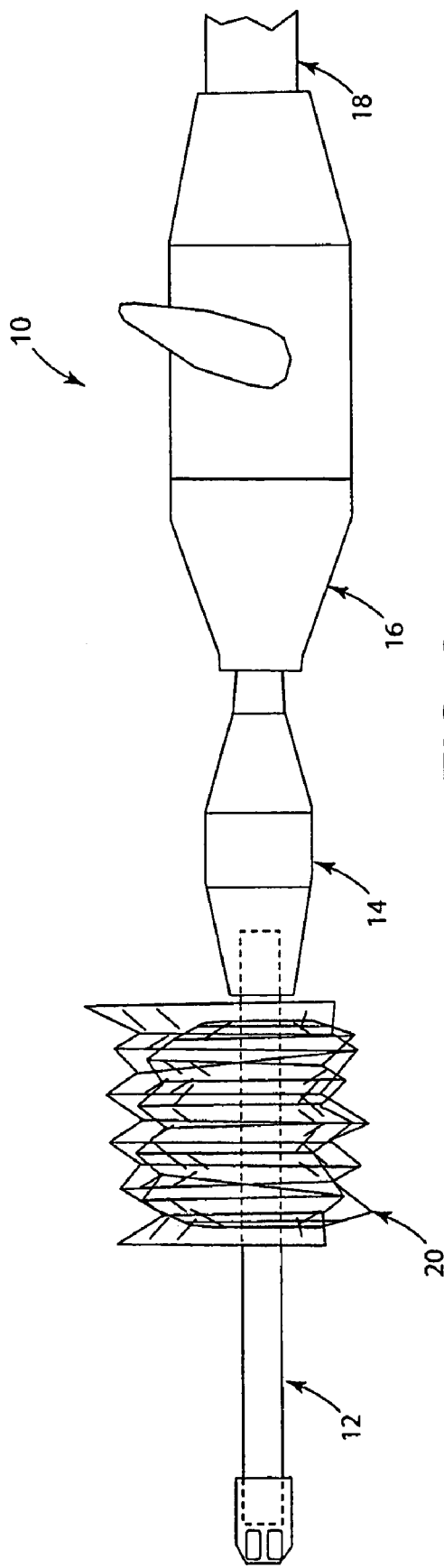
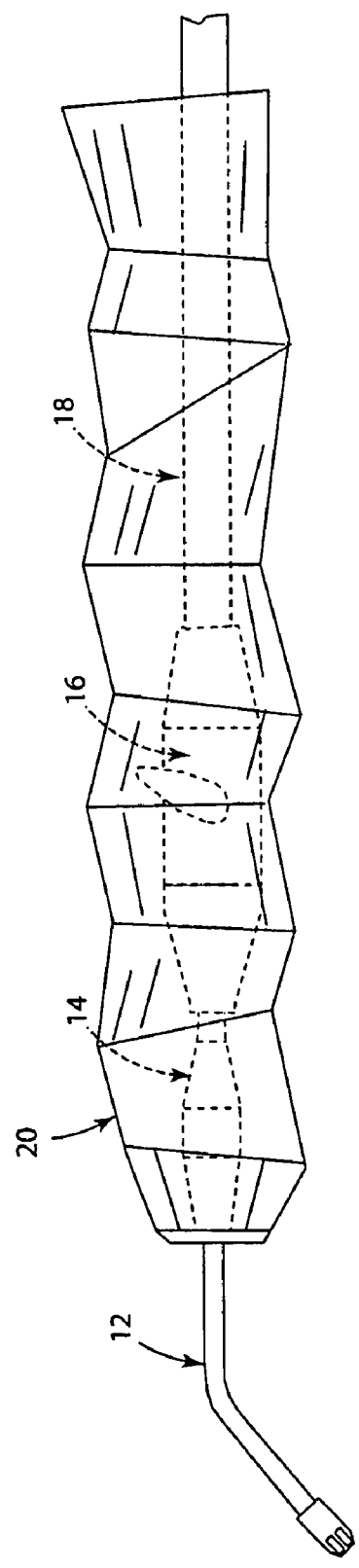
FIG. 1
FIG. 2

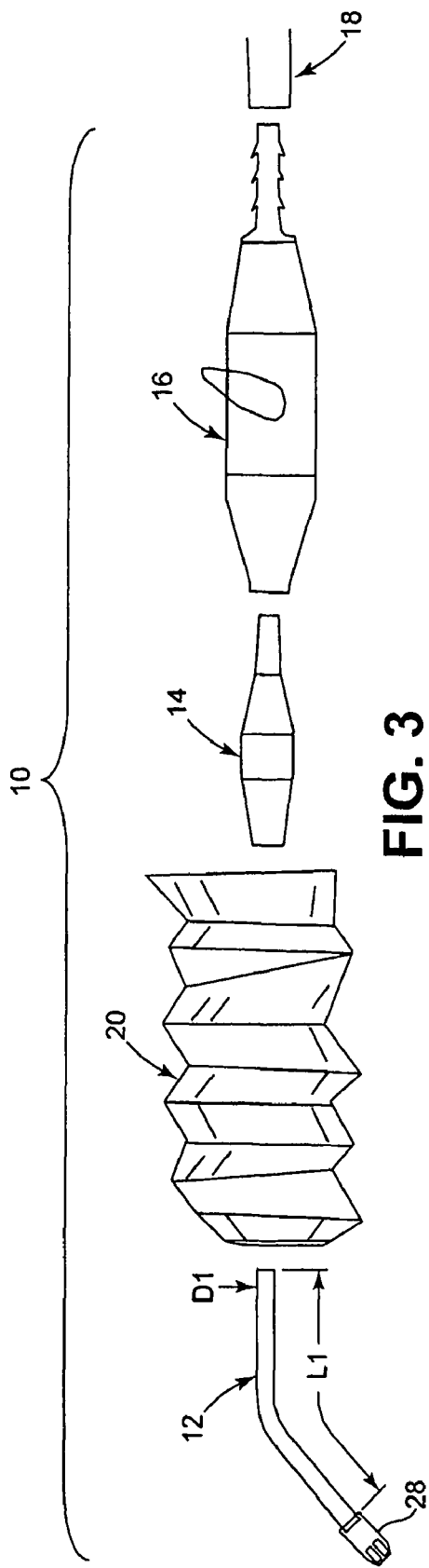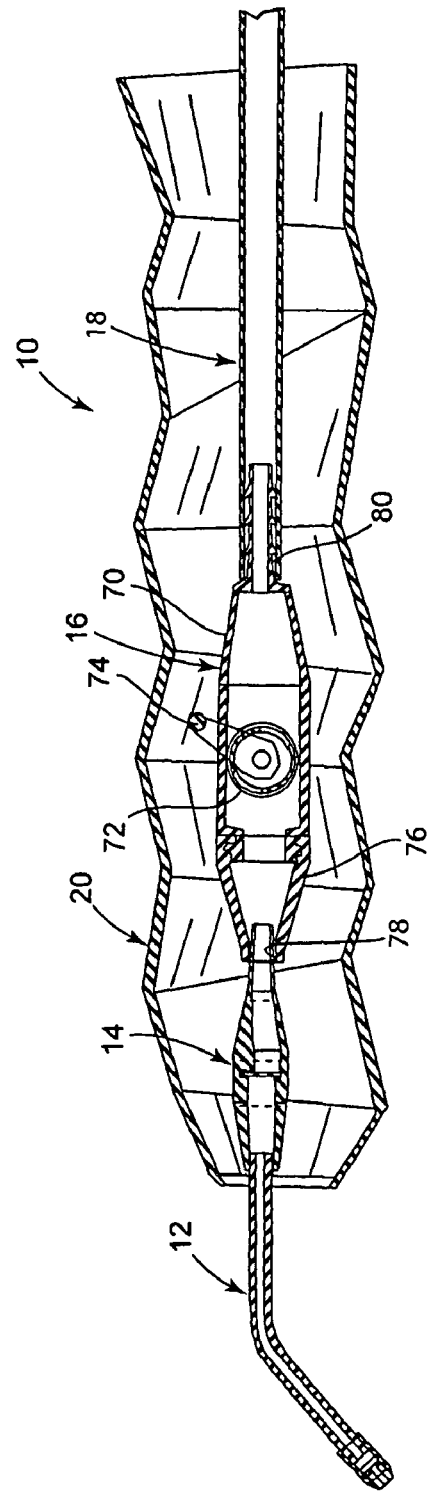

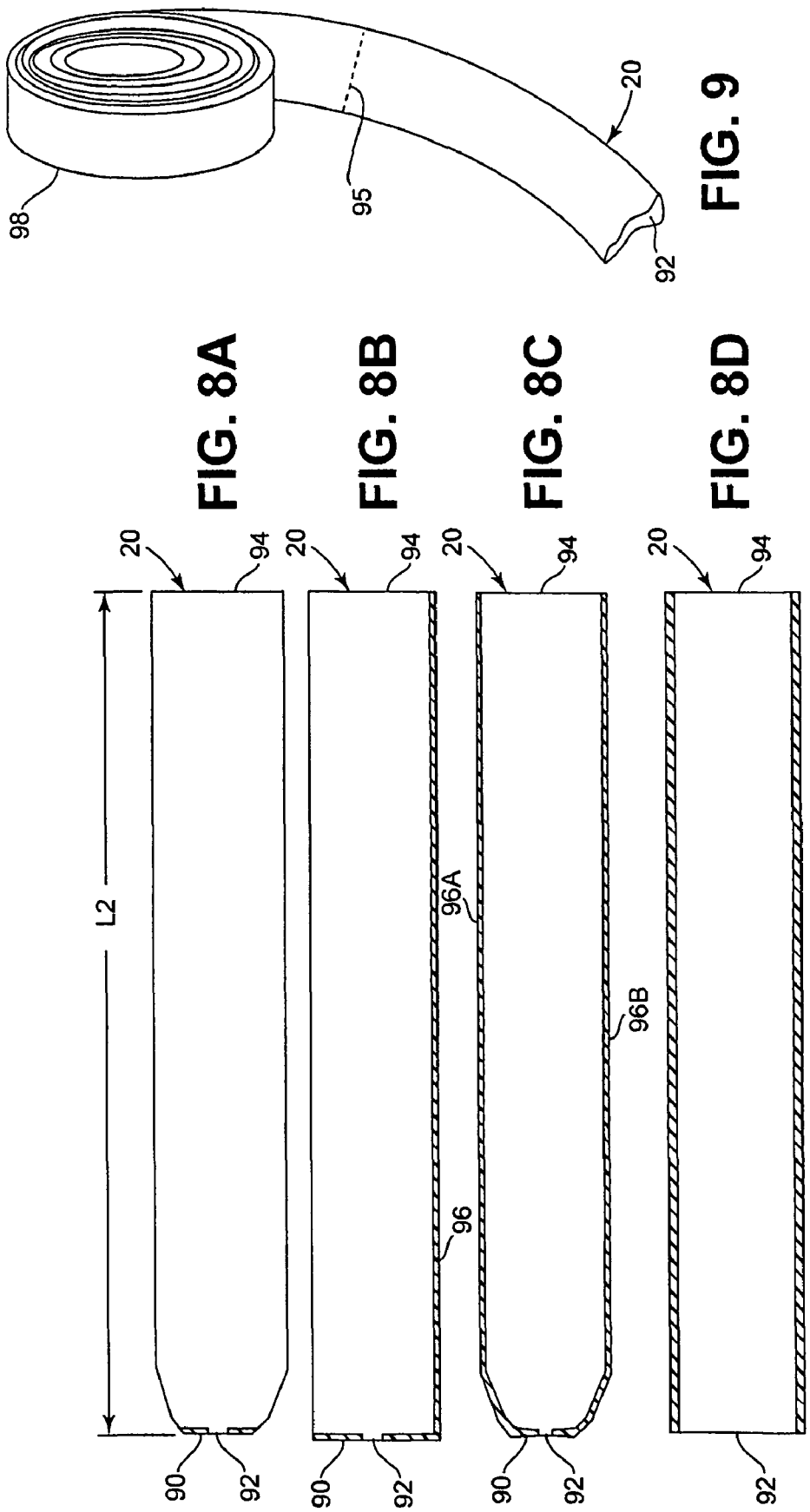

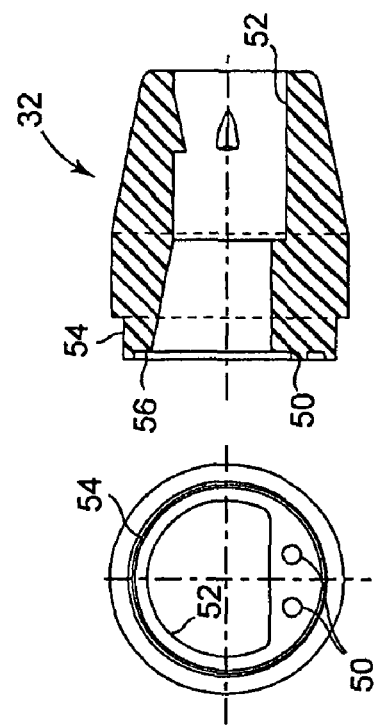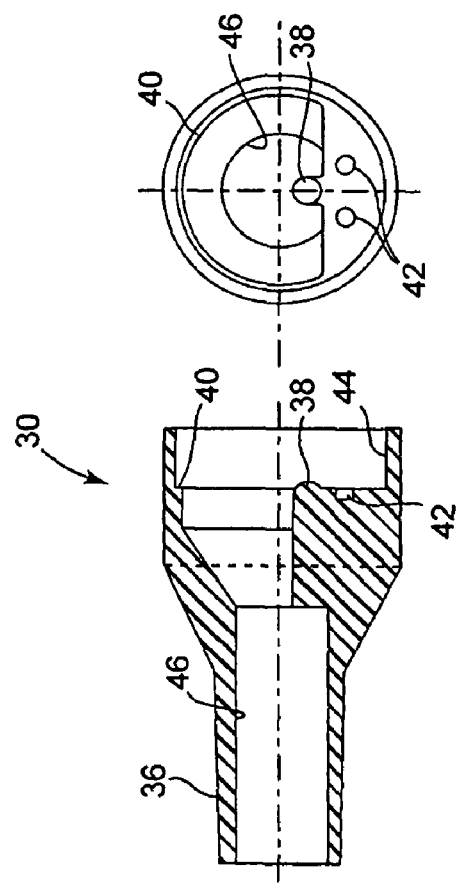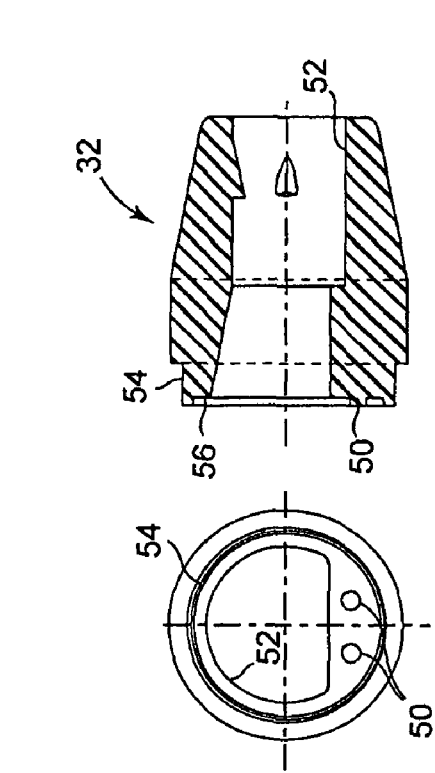
FIG. 14
FIG. 15
FIG. 13
FIG. 12

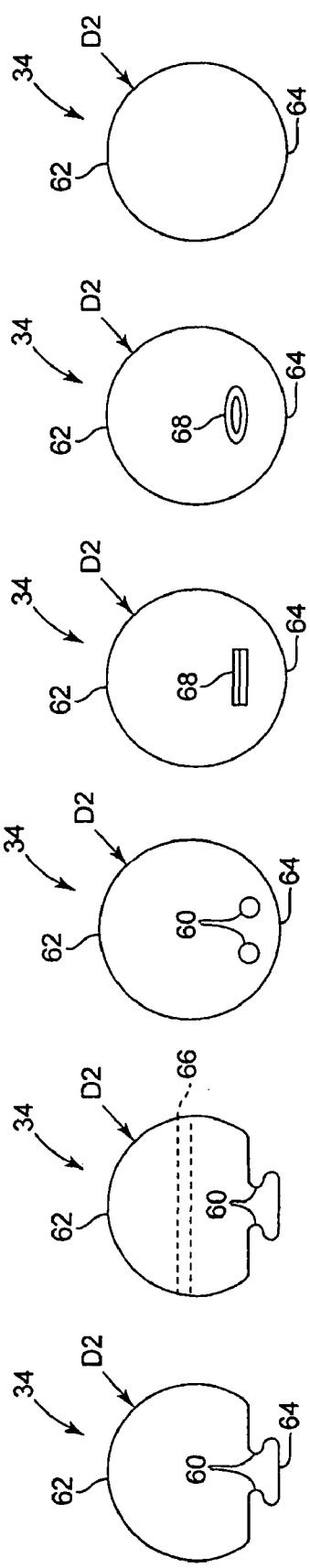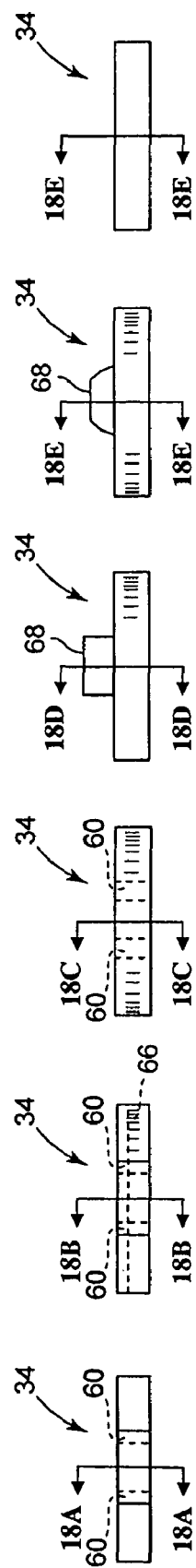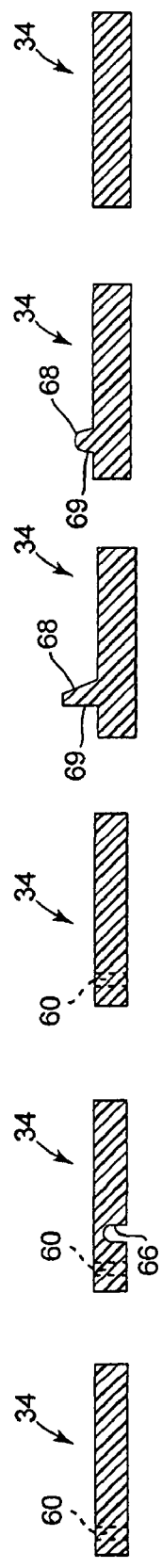

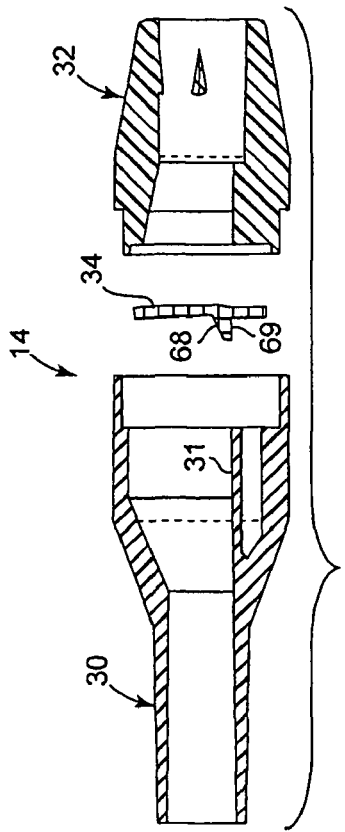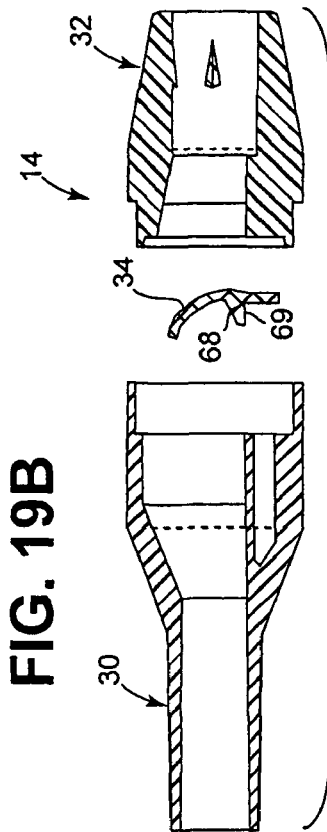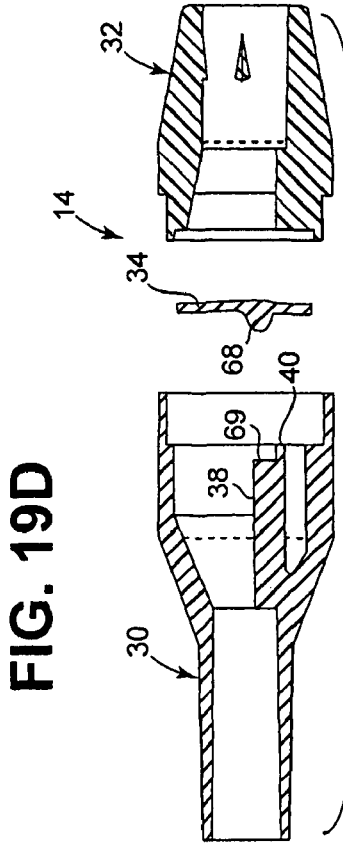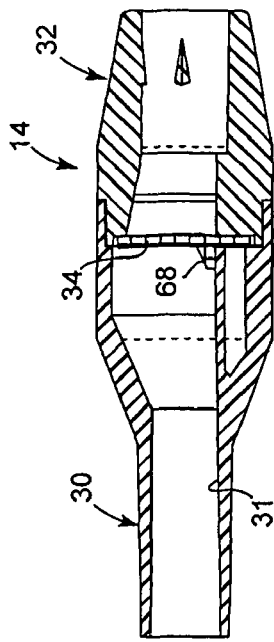

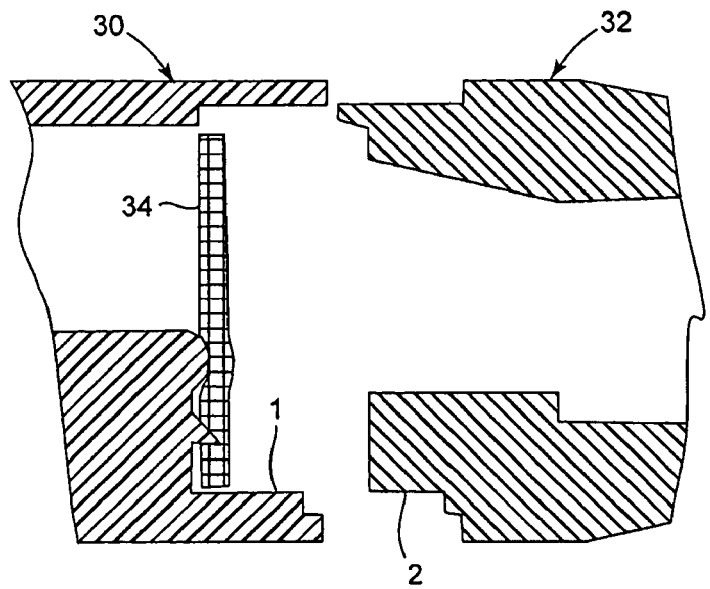
FIG. 20C
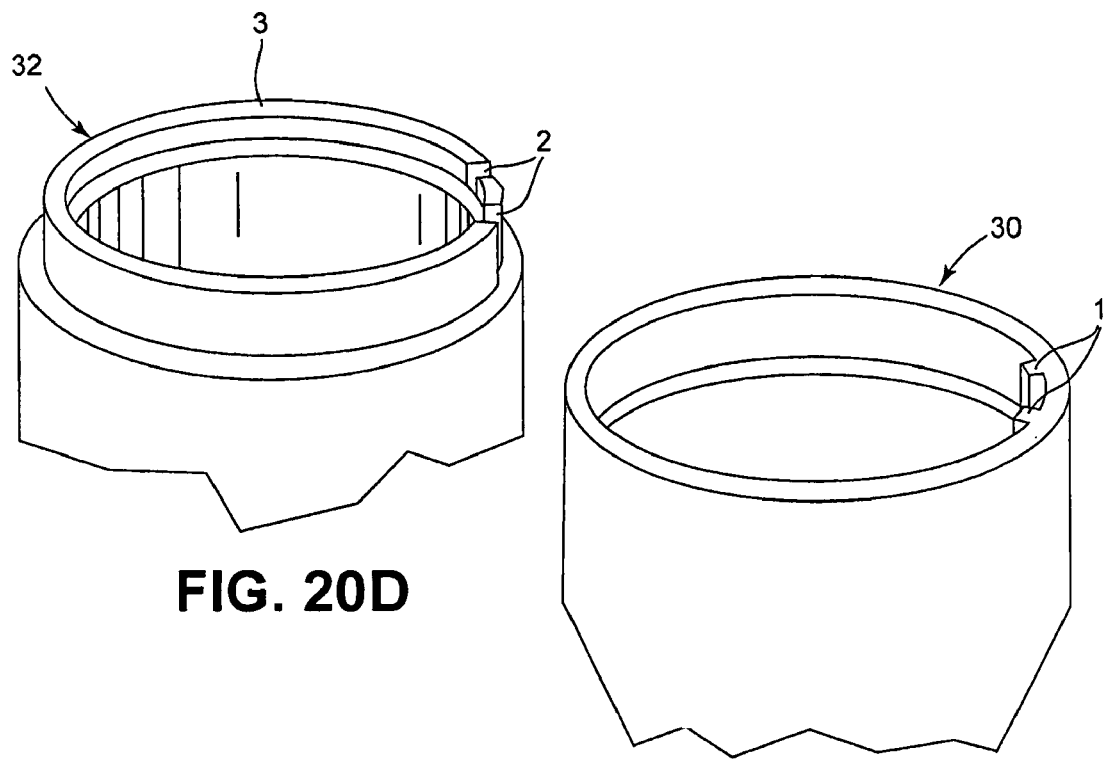
FIG. 20D
FIG. 20E

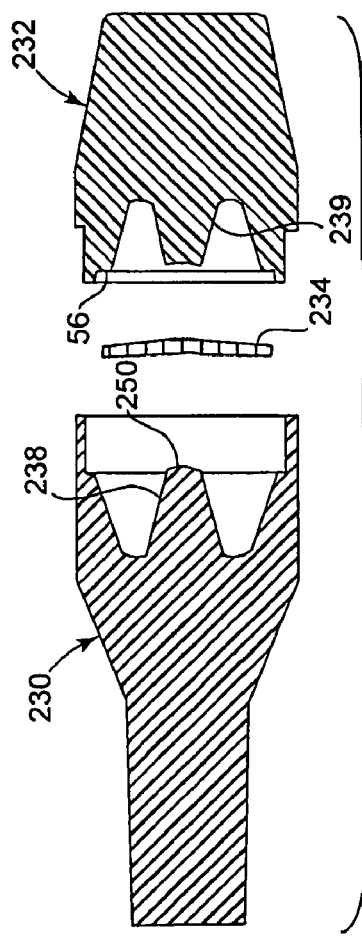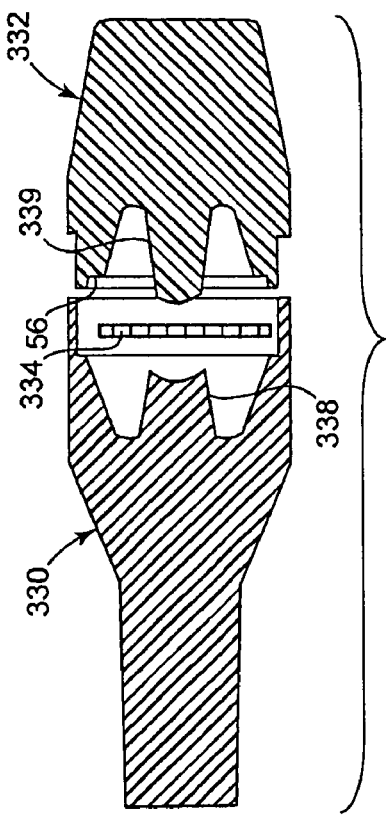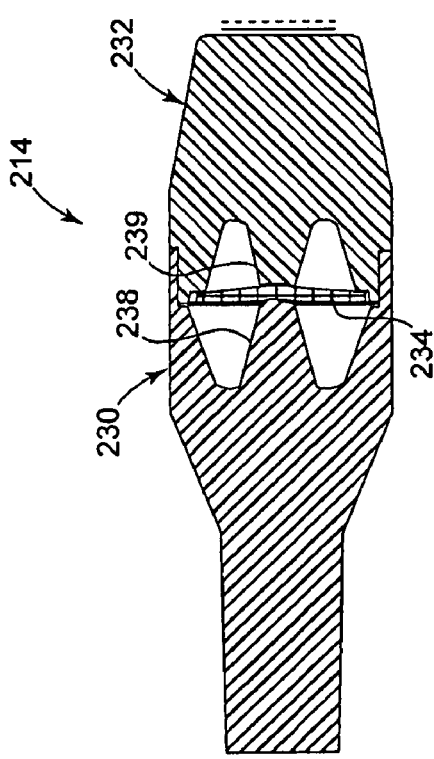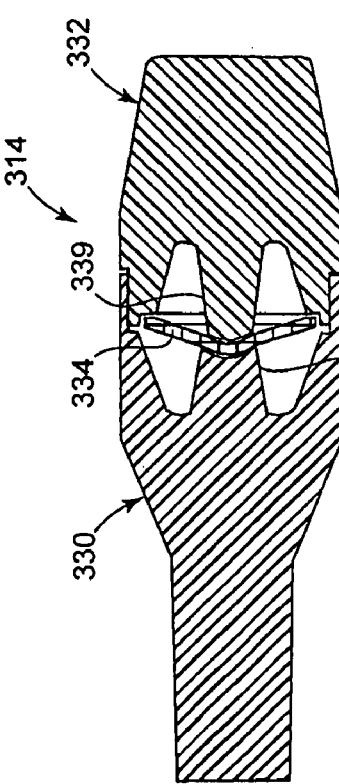

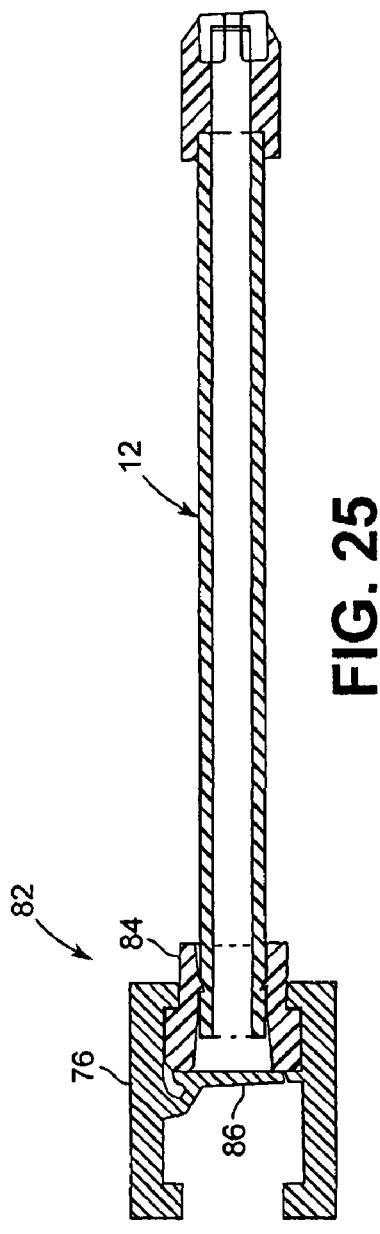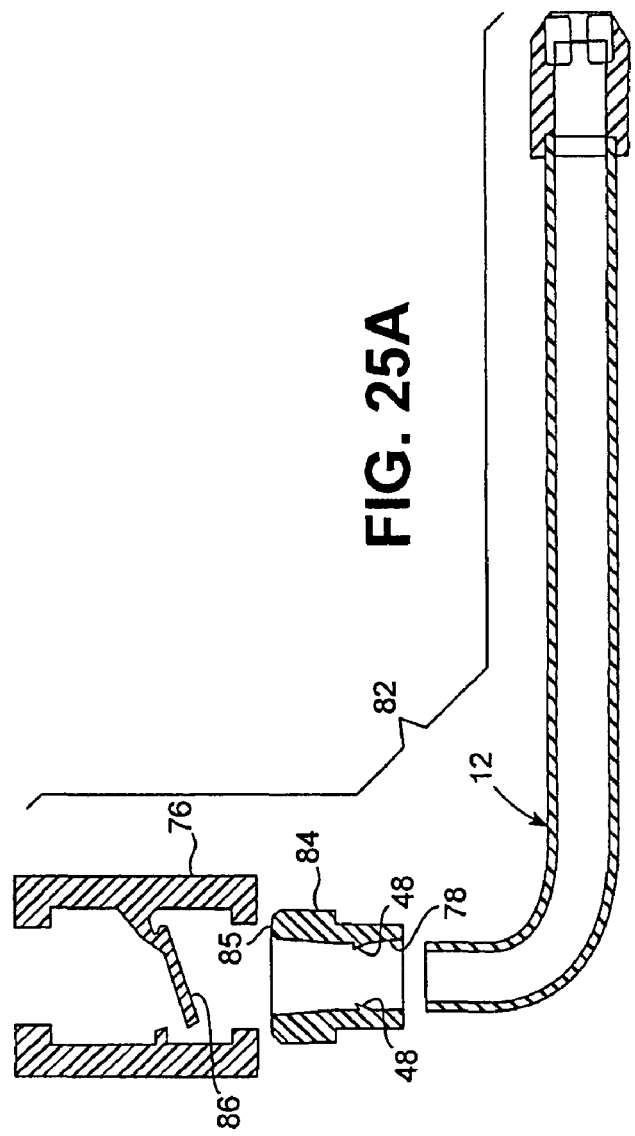

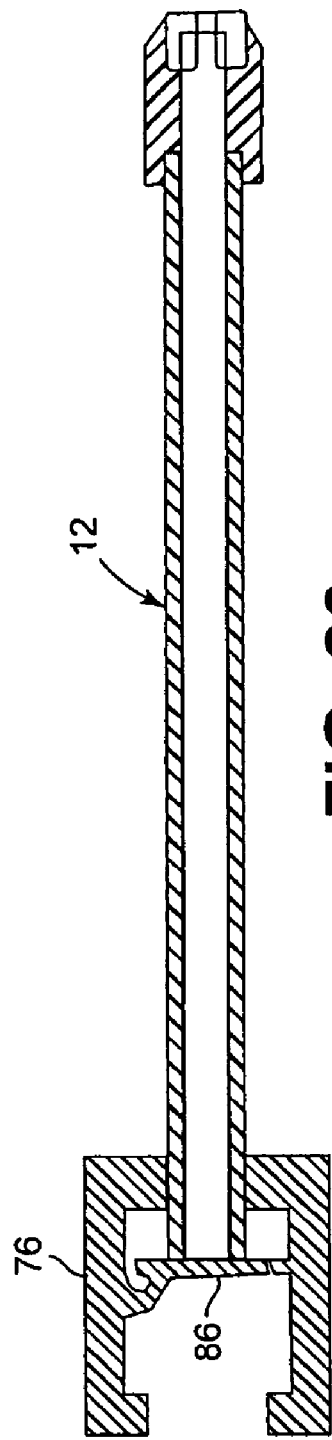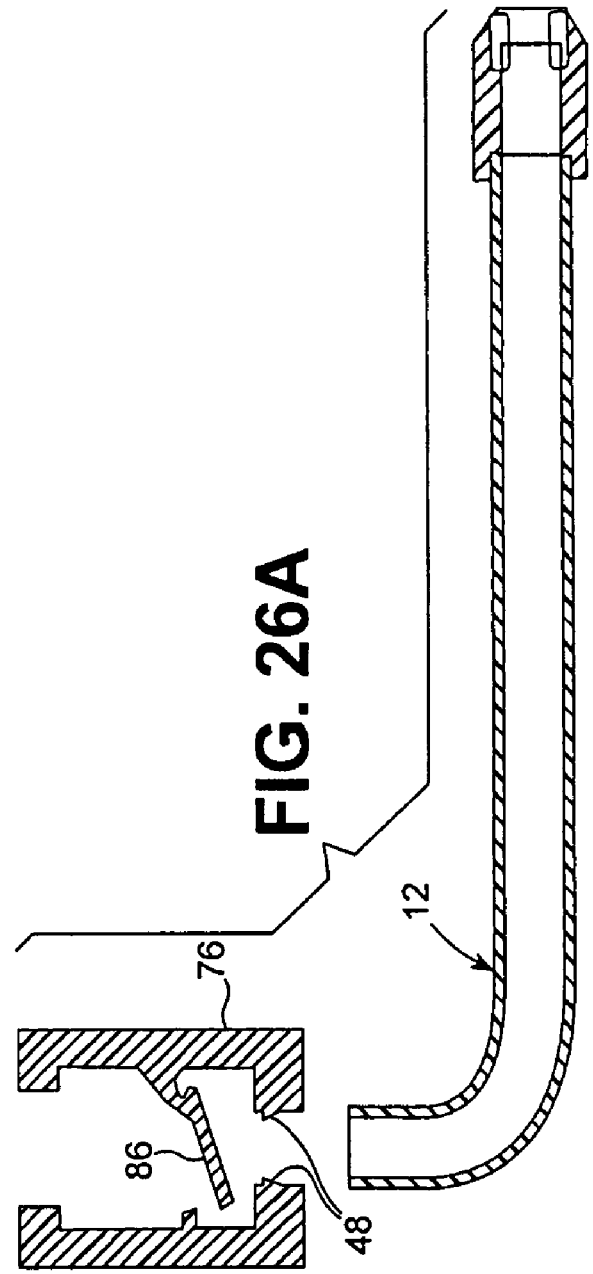

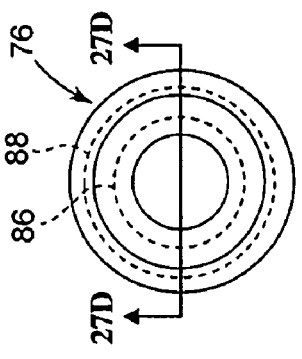
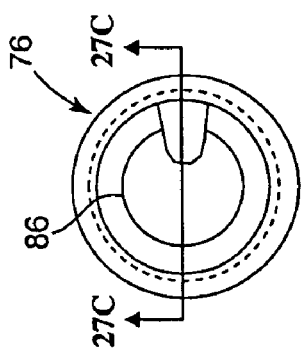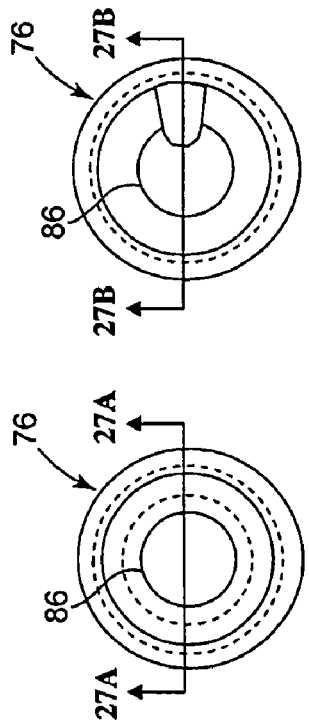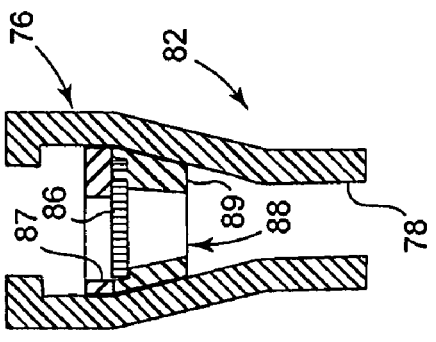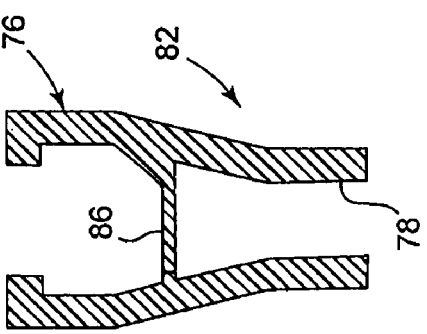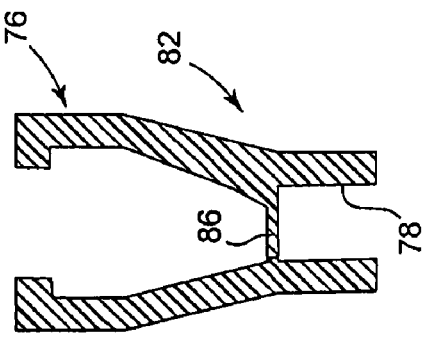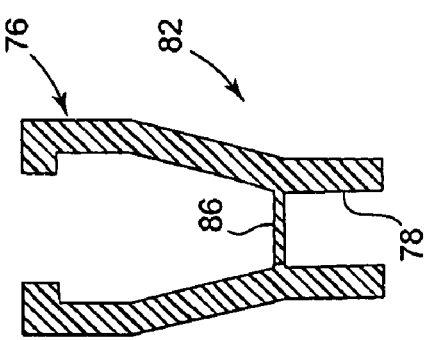

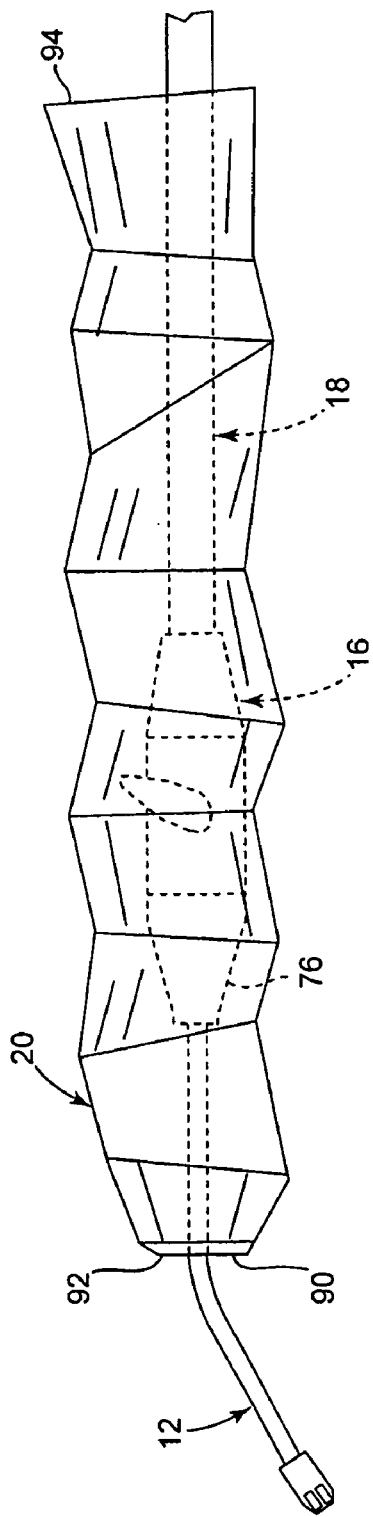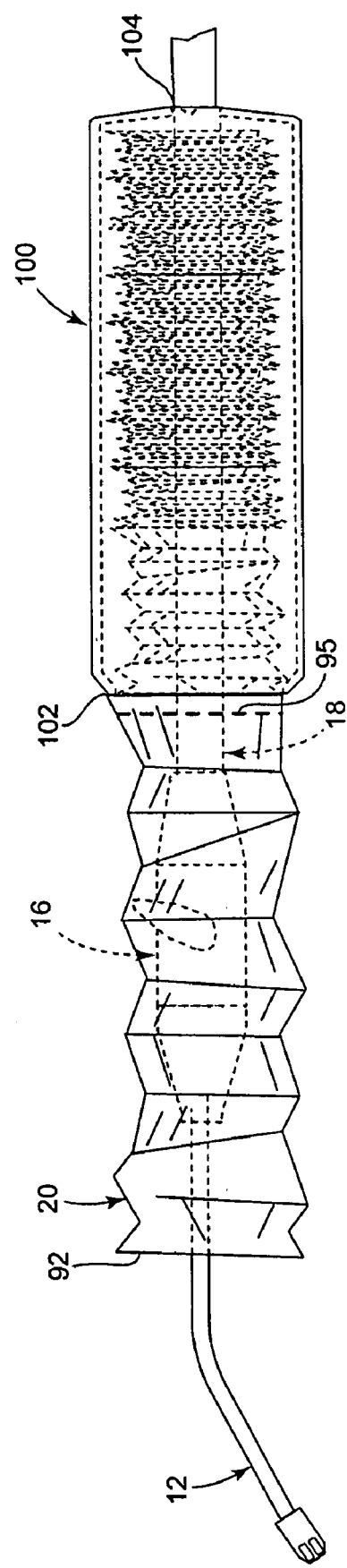

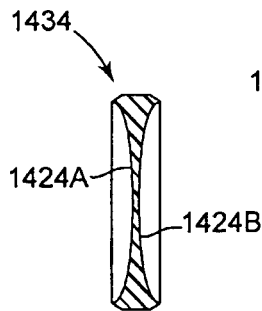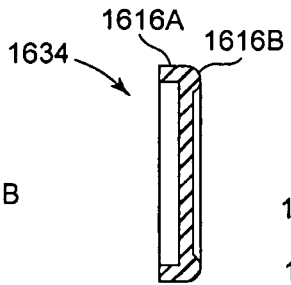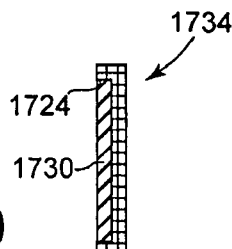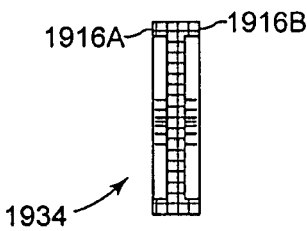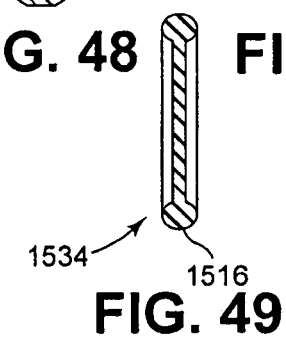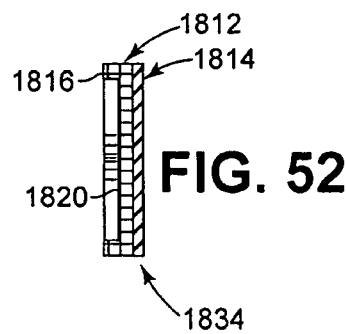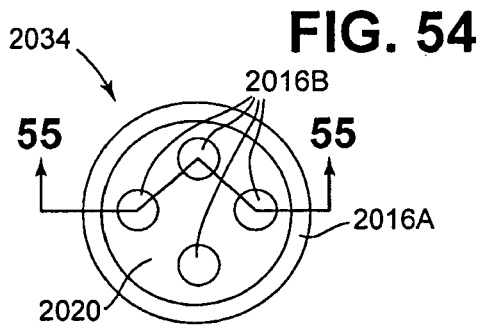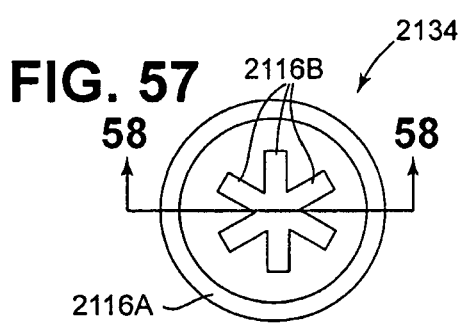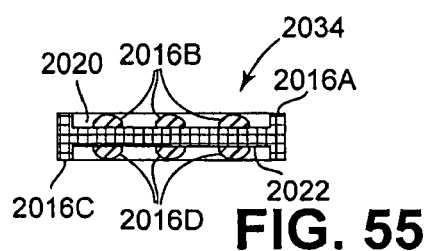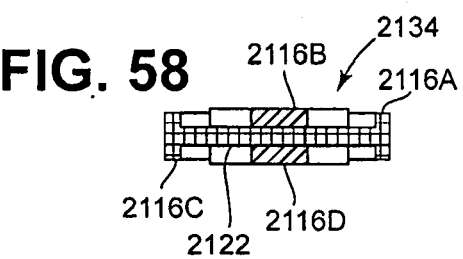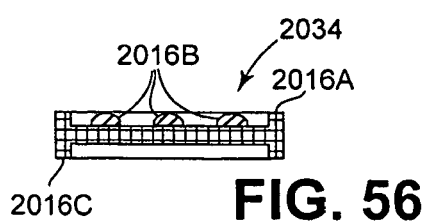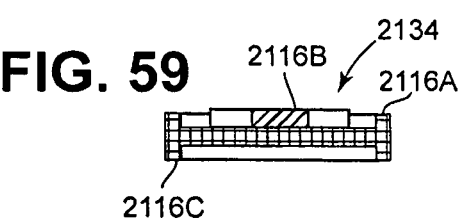

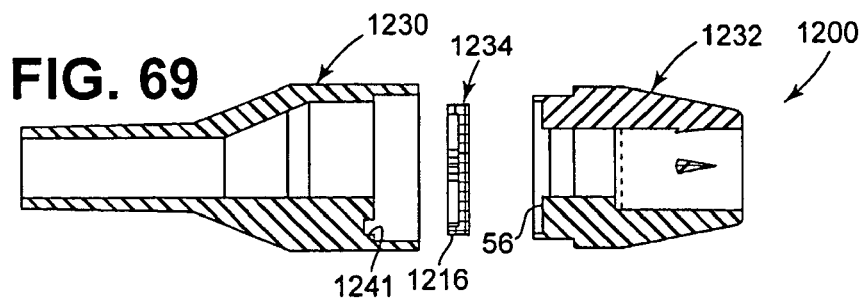
FIG. 69
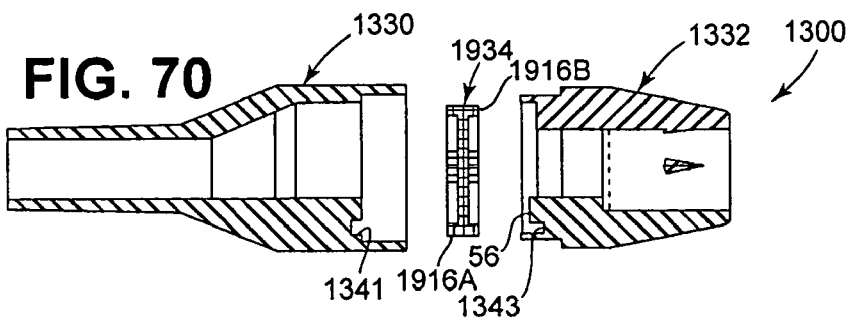
FIG. 70
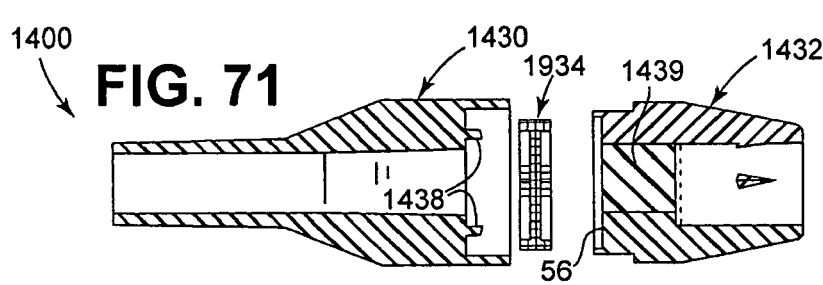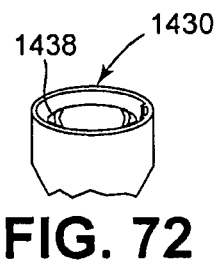
FIG. 71
FIG. 72
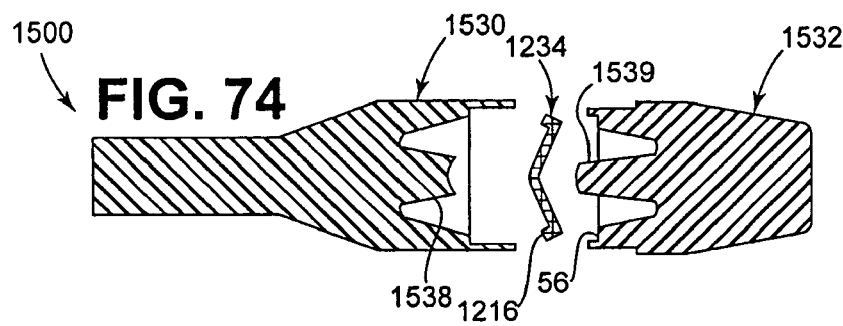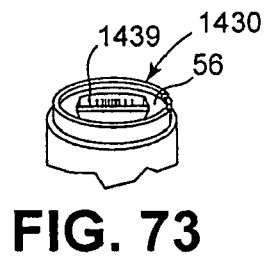
FIG. 74
FIG. 73
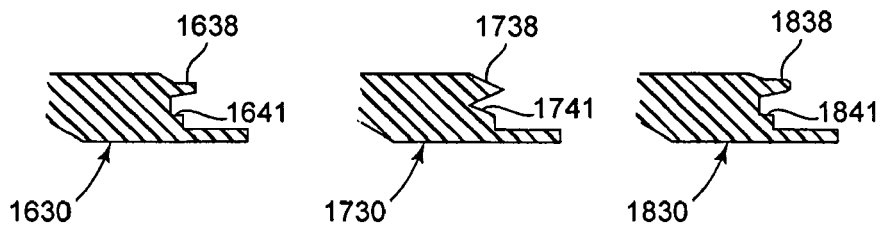
FIG. 75   FIG. 76   FIG. 77

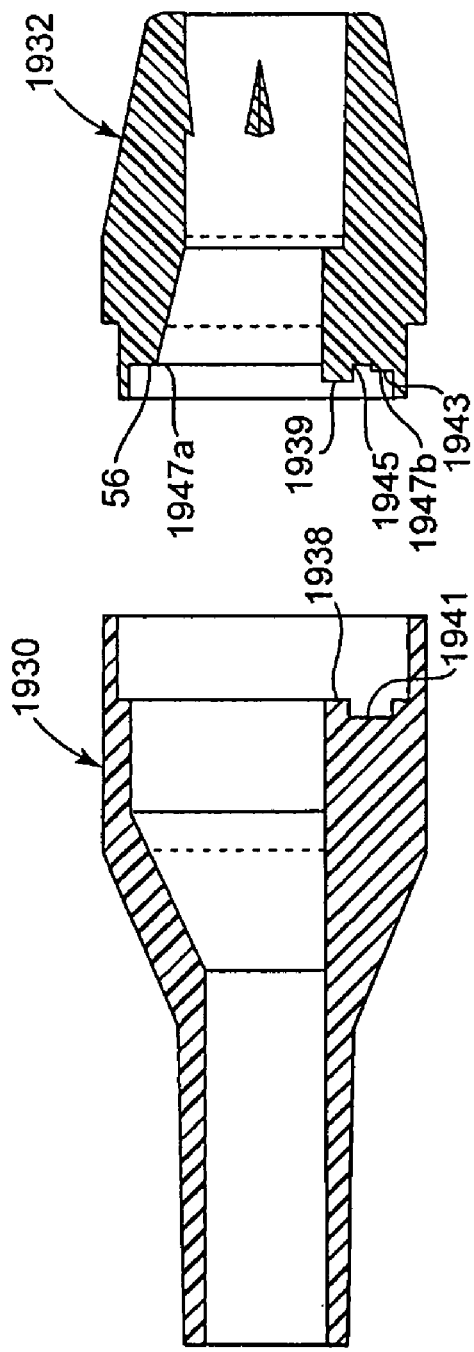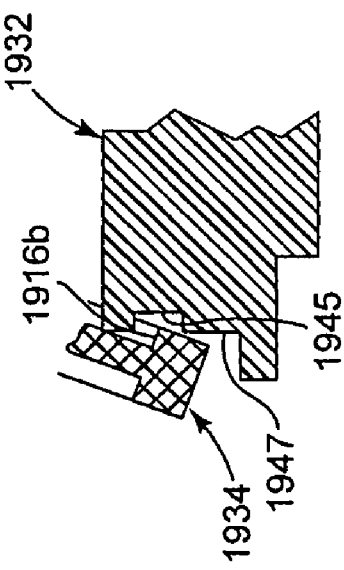

CHECK VALVE FLAP FOR FLUID INJECTOR

This application claims priority to and is a Continuation-In-Part of PCT US08/64302 filed on May 21, 2008 and titled IMPROVED CHECK VALVE FOR FLUID INJECTOR, and is a Continuation-In-Part of U.S. patent application Ser. No. 11/751,803, filed on May 22, 2007 and titled IMPROVED CHECK VALVE FOR FLUID INJECTOR, the entire disclosures of which are incorporated by reference.

TECHNICAL FIELD

The present disclosure generally relates to suctioning devices, and more particularly to medical and dental suctioning devices that are adapted to inhibit backflow of suctioned materials in the suctioning device.

BACKGROUND

Cross-contamination between patients, for example, dental patients, can occur when suctioning devices attached to vacuum lines are used to remove various bodily and/or externally introduced fluids. Although the disposable distal ends of these devices typically are changed between patients, the vacuum lines employed typically are not changed. Saliva, blood and other contaminants pass from the distal end into the vacuum line, where they can remain until arrival of the next patient. When a new distal end is inserted onto the vacuum line for a new patient, contaminants from the previous patient can backflow from the vacuum line into the distal end and enter the patient's mouth, for example. Clearly, with the growing incidence of AIDS and other communicable diseases, this is a situation to be avoided.

A number of prior art devices have attempted to prevent backflow and the resulting likelihood of cross-contamination between patients. U.S. Pat. Nos. 5,425,637 and 5,509,802 to Whitehouse, et al. and U.S Pat. No. 5,464,397 to Powers, Jr., which are incorporated herein by reference, disclose prior art attempts to prevent or at least minimize contaminant backflow and cross-contamination. The two Whitehouse patents disclose suction lines having vacuum-release apertures through a tubular sidewall of a saliva ejector tip. If a patient closes his or her lips around the tip, the vacuum-release aperture is said to prevent creation of a temporary high vacuum in the patient's mouth; the aperture also likely prevents stoppage of air and/or fluid, at least between the aperture and the rest of the system. The Powers, Jr. patent, on the other hand, appears to rely merely on a "tortuous path" within the device to substantially prevent backflow of bacteria.

However, as recent studies are believed to have shown, a boundary layer can form around the internal circumference of many currently used suctioning devices. The boundary layer is the portion of air and/or other fluid flowing in the immediate vicinity of the internal circumference. Flow within the boundary layer is severely reduced, even eliminated due to the forces of adhesion and viscosity caused by the internal circumference. Because suction within the boundary layer is reduced or eliminated, a "bio-film" can be created, allowing saliva, blood and other contaminants to flow by gravity, for example, from the main vacuum system of a dental office, through saliva ejector assemblies and into the mouths of patients.

It is believed that prior art suctioning devices do not adequately account for or address backflow caused by boundary layer conditions, and/or other conditions such as mouth-induced backflow suction. Prior art devices thus allow an unacceptably high likelihood of cross-contamination between patients. Clearly, a need has arisen for a solution to this problem.

SUMMARY

One aspect of the present disclosure relates to a backflow prevention system that can substantially prevent contaminant backflow from a vacuum device into a patient's mouth. The system in accordance with the present disclosure includes a fluid ejector tube for insertion into the patient's mouth and for removal of saliva, blood, etc. when a vacuum pressure is applied. A backflow prevention device receives fluid from the fluid ejector tube. Valve componentry disposed within the backflow prevention device includes a housing and a valve flap operably supported by the housing to engage the valve seat and prevent contaminant backflow upon release of the vacuum. Upon application of a vacuum condition, the valve flap moves to an open orientation to permit fluid flow away from the patient's mouth. The valve flap can include stiffening features that provide increased resistance to bending of the valve flap (i.e., increased rigidity or reduced flexibility) to help maintain the valve flap in a closed orientation until a threshold vacuum pressure condition exists. The stiffening features can be in the form of additional layers of material in the valve flap. The stiffening features can also include stiffening structures that extend from a surface of the valve flap or are embedded within the valve flap. Corresponding devices and methods provide similar advantages.

Another aspect of the present disclosure relates to valve flap configurations generally. The valve flap can include features that influence bending characteristics of the valve flap. For example, the valve flap can include recesses, protrusions, additional layers of material, and embedded material that can increases a resistance to bending in at least portions of the valve flap.

Another aspect of the present disclosure relates to a backflow prevention device that includes a distal housing portion, a proximal housing portion, and a valve member. The valve member is movable in the housing between open and closed orientations upon application of a vacuum pressure condition in the housing. At least one of the distal and proximal housing portions can include a protrusion that engages the valve flap to bias the valve flap into a particular orientation. At least one of the distal and proximal housing portions can include a recess feature sized to receive at least a portion of a stiffening structure of the valve flap. At least one of the distal and proximal housing portions can include at least one vent opening along a length thereof that bypasses the valve flap.

The above summary is not intended to describe each disclosed embodiment or every implementation of the inventive aspects disclosed herein. Figures in the detailed description that follow more particularly describe features that are examples of how certain inventive aspects may be practiced. While certain embodiments are illustrated and described, it will be appreciated that disclosure is not limited to such embodiments.

BRIEF DESCRIPTION OF THE DRAWINGS

FIG. 1 is a schematic side view of an example suction system in accordance with the present disclosure.

FIG. 2 is a schematic side view of the example suction system shown in FIG. 1 with the cover member positioned on the ejector tube.

FIG. 3 is schematic exploded side view of the example suction system shown in FIG. 1.

FIG. 4 is a schematic cross-sectional side view of the example suction system shown in FIG. 1.

FIGS. 8A-D are schematic cross-sectional side views showing example cover members in accordance with the present disclosure.

FIG. 9 is a schematic perspective view showing continuous length cover member in a rolled up state.

FIG. 12 is a schematic cross-sectional side view of the proximal housing portion of the backflow device shown in FIG. 10.

FIG. 13 is a schematic end view of the proximal housing portion shown in FIG. 12.

FIG. 14 is a schematic cross-sectional side view of the distal housing portion of the backflow device shown in FIG. 10.

FIG. 15 is a schematic end view of the distal housing portion shown in FIG. 12.

FIGS. 16A-F are schematic front views of several example valve flaps for use with the backflow devices shown herein.

FIGS. 17A-F are schematic bottom views of the example valve flaps shown in FIGS. 16A-E.

FIGS. 18A-F are schematic cross-sectional side views of the valve flaps shown in FIGS. 16A-E.

FIG. 19A is a schematic cross-sectional side view of another example backflow device in accordance with the present disclosure, wherein the valve flap is in a closed state.

FIG. 19B is a schematic exploded cross-sectional side view of the backflow device shown in FIG. 19A.

FIG. 19C is a schematic cross-sectional side view of the example backflow device shown in FIG. 19A, wherein the valve flap is in an open state.

FIG. 19D is a schematic exploded cross-sectional side view of the backflow device shown in FIG. 19C.

FIG. 20C is a schematic exploded cross-sectional side view of the backflow device shown in FIG. 20A and further including a rib and channel connection arrangement on the proximal and distal housing portions.

FIG. 20D is a schematic perspective view of the distal housing portion of the backflow device shown in FIG. 20C.

FIG. 20E is a schematic perspective view of the proximal housing portion of the backflow device shown in FIG. 20C.

FIG. 21A is a schematic cross-sectional side view of another example backflow device in accordance with the present disclosure, wherein the valve flap is in a closed state.

FIG. 21B is a schematic exploded cross-sectional side view of the backflow device shown in FIG. 21A.

FIG. 24A is a schematic cross-sectional side view of another example backflow device in accordance with the present disclosure, wherein the biasing protrusion includes a connection protrusion.

FIG. 24B is a schematic exploded cross-sectional side view the example backflow device shown in FIG. 24B.

FIG. 24C is a schematic cross-sectional side view of another example backflow device in accordance with the present disclosure, wherein biasing protrusion and retention protrusion are shaped to bias the valve flap in a closed state.

FIG. 24D is a schematic exploded cross-sectional side view of the example backflow device shown in FIG. 24D.

FIG. 25 is a schematic cross-section side view of an example assembly in accordance with the present disclosure, wherein the assembly includes an ejector tube and an ON/OFF valve boot, the boot including a backflow valve member.

FIG. 25A is a schematic exploded cross-sectional side view of the assembly shown in FIG. 25.

FIG. 26 is a schematic cross-section side view of another example assembly in accordance with the present disclosure, wherein the assembly includes an ejector tube and an ON/OFF valve boot, the boot including a backflow valve member.

FIG. 26A is a schematic exploded cross-sectional view of the assembly shown in FIG. 26.

FIGS. 27A-D are schematic cross-sectional side views of several example ON/OFF valve boots having a backflow valve member in accordance with the present disclosure.

FIGS. 28A-D are schematic cross-sectional end views of the ON/OFF valve boots shown in FIGS. 27A-D.

FIG. 29 is a schematic side view of another example assembly in accordance with the present disclosure, wherein the assembly includes an ON/OFF valve, an ejector tube, and a cover member.

FIG. 30 is a schematic side view of another example assembly in accordance with the present disclosure, wherein the assembly includes an ON/OFF valve, an ejector tube, and a cover member, the cover member being drawn from a continuous cover member that is housed proximal of the ON/OFF valve.

FIGS. 44-53 are schematic cross-sectional side views of several example valve flap configurations in accordance with principles of the present disclosure.

FIG. 54 is a schematic front view of another example valve flap configuration having a plurality of round stiffening members.

FIGS. 55-56 are schematic cross-sectional side views of the valve flap shown in FIG. 54.

FIG. 57 is a schematic front view of another example valve flap configuration having a plurality of liner intersecting stiffening members.

FIGS. 58-59 are schematic cross-sectional side views of the valve flap shown in FIG. 57.

FIGS. 69-71 and 74 are schematic cross-sectional side views of several example backflow prevention assemblies in accordance with principles of the present disclosure.

FIGS. 72-73 are schematic perspective view of the proximal and distal housing portions shown in FIG. 71.

FIGS. 75-77 are schematic cross-sectional side views of portions of further example proximal housing portion constructions in accordance with principles of the present disclosure.

FIG. 78 is a schematic cross-sectional side view of another example set of proximal and distal housing portion in accordance with principles of the present disclosure.

FIG. 79 is a schematic cross-sectional side view of a portion of the distal housing member shown in FIG. 78 and a portion of a valve flap.

DETAILED DESCRIPTION

Figure 7:
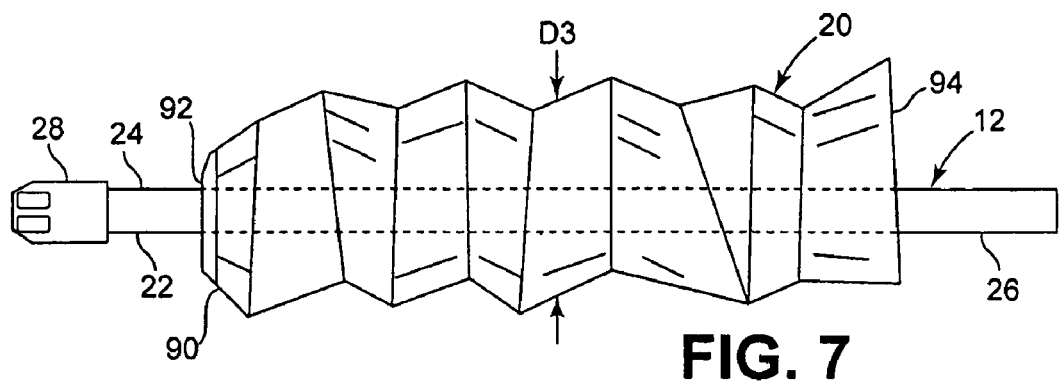
FIG. 7 is a schematic side view of another example assembly in accordance with the present disclosure that includes an ejector tube and cover.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The following discussion is intended to provide a brief, general description of a suitable environment in which the invention may be implemented. Although not required, the invention will be described in the general context of vacuum suction devices, for example, a dental saliva ejector device. The structure, creation, and use of some example dental fluid ejector devices are described hereinafter.

The example embodiments disclosed herein have wide application to a number of medical procedures and environments. Suction is often used in dental applications, as described above. Suctioning devices are also typically used to drain fluid and remove blood from many surgical environments, aid in respiration, and aid in a number of other medical and surgical procedures. Additionally, suctioning devices in which cross-contamination is undesirable are used in non-medical and non-surgical environments, such as in some types of liquid soap dispensers where preventing backflow of a fluid is required. Therefore, while most of the embodiments described with reference to the attached figures are directed to dental devices and applications, many other applications and related embodiments are envisioned.

The Example Suction Assemblies of FIGS. 1-24D

Several example suction assemblies 10 are described now with reference to FIGS. 1-24D. The suction assembly 10 includes an ejector tube assembly 12, a backflow prevention assembly 14, an ON/OFF valve assembly 16, a vacuum hose 18, and a cover member 20. These features are shown in the exploded view of FIG. 3 and in further detail in the cross-sectional view of FIG. 4. The features 12, 14, 16, 18, 20 can be combined as separate subassemblies that are coupled together at the point of use where, for example, a patient is being treated by the suction assembly 10. In one example, the ejector tube assembly 12 and cover member 20 are arranged as a subassembly that is later connected to the backflow prevention assembly 14, or in alternative embodiments connected directly to the ON/OFF valve assembly 16. In another example arrangement, the ejector tube assembly 12, backflow prevention assembly 14, and cover member 20 are provided as a subassembly that is removably engaged with the ON/OFF valve assembly 16. Other subassembly arrangements are possible, some of which are described in further detail below.

The ejector tube assembly 12 includes an ejector tube 22, having distal and proximal ends 24, 26, an outer diameter D1, a length L1, and an ejector tip 28 (see FIG. 3). The ejector tube 22 can be referenced as, for example, a fluid or liquid ejector tube, a saliva ejector tube, a particle ejector tube, or a fluid source tube. The ejector tube 22 can have a contoured shape. The contoured shape of the ejector tube 22 can be preformed. In some arrangements, the ejector tube assembly 12 can include a stiffening member such as a wire that extends along at least a portion of the length of the tube 22 that provides adjustability of the contoured shape and retention of that shape due to the inherent stiffness of the stiffening member. The outer diameter D1 is typically sized to provide insertion of the proximal end 26 into the distal end of the backflow prevention assembly 14. The ejector tip 28 can have various constructions that provide proper fluid flow into the ejector tube assembly 12.

The backflow prevention assembly 14 includes a proximal housing portion 30, a distal housing portion 32, and a valve flap 34. Other example backflow prevention assemblies are disclosed in co-owned U.S. Pat. No. 6,203,321, which is incorporated herein by reference. Many of the embodiments disclosed in U.S. Pat. No. 6,203,321 require a plurality of components used in the valving structure within the backflow prevention assembly. Further, many of the examples disclosed in U.S. Pat. No. 6,203,321 include valving components that are molded, which can increase the complexity and cost associated with generating those valving components.

Referring now to FIGS. 10-21B, the proximal housing portion 30 includes a neck portion 36, a biasing protrusion 38, a first mating surface 40, a pair of connection recesses 42, a second mating surface 44, and a flow orifice 46. The proximal housing portion 30 can also include a plurality of barbed members (e.g., barbs 48 that are shown positioned interior of the distal housing portion 32) that can be positioned on an exterior of the neck portion 36 to help retain the backflow prevention assembly 14 in engagement with the ON/OFF valve assembly 16.

The biasing protrusion 38 is positioned vertically above the connection recesses 42. A distal end of the biasing protrusion 38 extends distally in the axial direction beyond the first mating surface 40 (see FIG. 12). The biasing protrusion 38 exerts an axially directed force upon the valve flap 34 when the backflow prevention assembly 14 is assembled.

The distal housing portion 32 includes a pair of connection protrusions 50, a tube orifice 52, a mating member 54, and a valve seat 56 (see FIG. 14). The connection protrusions 50 are sized to extend through the valve flap 34 and into the connection recesses 42 by the proximal housing portion. The tube orifice 52 is sized to receive the proximal end of the ejector tube 22. The distal housing portion 32 can further include a plurality of barbs 48 that are positioned along the tube orifice surface 52. The barbs 48 are configured to engage an outer surface of the ejector tube 22 to provide an improved connection between the ejector tube assembly 12 and backflow prevention assembly 14. The mating member 54 is sized to engage the first and second mating surfaces 40, 44 of the proximal housing portion 30. The outer diameter surface of the mating member 54 can engage the second mating surface 44 with an interference fit that promotes retention of the proximal and distal housing portions together.

In some arrangements, a connector, fastener, adhesive, or other connecting means can be used to secure the proximal and distal housing portions 30, 32 together in a permanent connection or in a connection arrangement in which the proximal and distal housing portions releaseably engaged with each other. In one example, a latching arrangement can be used on the mating surfaces 40, 44 to provide a snap-fit connection between the housing portions 30, 32. An example arrangement includes a pair of protrusions (not shown) are positioned on the surface 40 at 180° spaced apart locations. The protrusions are configured to engage within a pair of recesses (not shown) positioned on the surface 44 also at 180° spaced apart locations, wherein engagement of the protrusions (not shown) in the recesses (not shown) provide a snap-fit connection between the housing portions 30, 32. The snap-fit connection can be permanent, in that the connection cannot be disconnected without permanent damage to the housing portions 30, 32, or releasable in construction to permit disconnecting of the housing portions 30, 32 without permanent damage being caused.

The use of a single protrusion/recess pair or at least three protrusion/recess pairs can be used to provide a desired connection between the housing portions 30, 32. The protrusion/recess pair can have any configuration and structure that limits relative axial movement of the housing portions 30, 32 after the connection between the protrusion and recess are made.

Further, a snap-fit connection such as the protrusion/recess configuration described above, can be used in combination with other connecting and/or aligning features. Referring to FIGS. 20C-E, an example rib 1 and channel 2 arrangement is shown. The rib 1 is positioned on the proximal housing portion 30 and the channel 2 is positioned on the distal housing portion 32. The rib 1 and channel 2 are arranged in an axial direction. The channel 2 is exposed on a proximal end 3 of the distal housing portion 32. The channel 2 and rib 1 can be positioned at any radial location around the circumference of the housing portions 30, 32. The channel 2 and rib 1 can be exchanged to be on the opposite housing portion 30, 32.

More than one pair of channel/rib features can be included on any given pair of housing portions 30, 32. For example, a pair of channel/rib features can be included for each protrusion/recess pair included on a pair of housing portions 30, 32. In one example, a pair of channel/rib features can be positioned radially adjacent to a protrusion/recess pair on the housing portions 30, 32. The channel 2 and rib 1 can be sized to provide an interference fit there between when engaged with each other. Engagement of the channel 2 and rib 1 can reduce axial, radial, and rotational movement of the housing portions 30, 32 when the housing portions 30, 32 are connected together with the valve flap 34 captured there between.

Other alignment features besides a pair of channel/rib features can be used to help align the housing portions 30, 32 relative to each other when connecting the housing portions 30, 32 together.

The valve flap 34 includes a pair of connection apertures 60, a top end portion 62, a bottom end portion 64, and a diameter D2. The valve flap 34 is sized with a thickness that permits the connection protrusions 50 to extend through the connection aperture 60 and into the connection recesses 42 with the valve flap 34 positioned between the first mating surface 40 of the proximal housing portion 30 and the valve seat 56 of the distal housing portion 32. The diameter D2 of the valve flap 34 is sized no greater than the maximum internal diameter of the valve seat 56.

In other arrangements, the connection protrusions 50 do not extend completely through the connection recesses 42. The connection protrusions 50 can be configured to extend only partially through the thickness of valve flap 34. In other arrangements, the valve flap 34 does not include connection apertures and the connection protrusions 50 are configured to apply a compression force against the valve flap 34 to help retain the valve flap in place. The connection protrusions 50 can have a construction that promotes either concentrated point contact (i.e., a "pinching" contact) with the valve flap 34 or self-penetration of the valve flap 34. FIGS. 20A-C and 24B-C illustrate barb-shaped connection protrusions 50, 250 that engage a valve flap 34, 234 (e.g., see example valve flap 34 shown in FIG. 16F that does not include connection recesses 42). The connection protrusions 50, 250 of FIGS. 20A-C and 24B-C can also be used with a valve flap 34 having connection recesses 42 aligned with the connection protrusions 50, 250. One example connection recess 42 (not shown) for use with connection protrusions 50, 250 shown in FIGS. 20A-C and 24B-C has a shape and size that substantially matches the barb shape of the connection protrusion 50. In still further arrangements, different numbers of connection protrusions and connection recesses can be used to help retain the valve flap. For example, any number from 0 to 3 or more connection protrusions and connection recesses can be used. The connection protrusions 50 can be also be referenced as valve retention members or pins.

The valve flap 34 can have many different configurations (e.g., size and shape) for use with the example proximal and distal housing portions 30, 32 shown in the figures, or variations of those housing portions. FIGS. 16A-18F illustrate several example valve flap configuration. The valve flaps 34 shown in FIGS. 16A-C, 17A-C and 18A-C include contoured cutouts or connection apertures 60 along the bottom end portions 64 of the valve flap 34. The addition of a cutout in the example shown in FIGS. 16A-B can provide easier assembly of the backflow prevention assembly, including insertion of the connection protrusions 50 through the valve flap 34 and into the connection recesses 42. FIG. 16C illustrates an example in which the connection apertures 60 are formed holes at the bottom end portion 64 of the valve flap 34.

The size and shape of the connection apertures 60 can vary as desired to provide, for example, an interference fit over the connection protrusions 50 to ensure tight tolerances. In some arrangements, the connection apertures 60 can have a size greater than the connection protrusions 50 to promote easier assembly and, for example, to ensure free movement of the valve flap 34 relative to the proximal and distal housing portions 30, 32. The contoured cutouts and connection apertures 60 shown in FIGS. 16A-C can be formed using a variety of techniques such as, for example, stamping and molding.

FIGS. 16D-E, 17D-E and 18D-E illustrate some example valve flap configurations that include a protrusion member 68. The protrusion 68 shown in FIG. 16C extends proximally and includes a bottom surface 69 that engages a bottom interior floor surface 31 of the proximal portion 30 (see FIGS. 19A-D). The protrusion 68 provides a function similar to the function of the biasing protrusion 38, but is positioned on the valve flap 34 rather than on the proximal portion 30. The protrusion 68 applies a biasing force against the valve flap 34 in a distal direction to bias the valve flap 34 into a closed position shown in FIG. 19A until a sufficient vacuum force is applied to move the valve flap 34 into the open position shown in FIGS. 19C-D. Typically, the biasing protrusion 38 and protrusion 68 of FIG. 16D are not present in the same backflow prevention assembly 14. Either one of the biasing protrusion 38 (and 138 described below) and the protrusion 68 can be referred to and functional as a valve protrusion that helps bias the valve flap 34 into the closed position.

FIG. 16E illustrates a protrusion 68 having a different construction than the protrusion 68 shown in FIG. 16D. The protrusion 68 of FIG. 16E is configured for use with a biasing protrusion 38 as shown in FIGS. 21A-B. The biasing protrusion 38 in FIGS. 21A-B is truncated to provide a recess 69 adjacent to the first mating surface 40 and the bottom interior floor surface 31 to receive the protrusion 68. When the protrusion 68 is positioned in the recess 69, the protrusion 68 is able to apply a biasing force against the valve flap 34 to hold the valve flap 34 in the closed position shown in FIG. 21A-B.

Many other constructions and combinations of features are possible for the protrusion 68, proximal portion 14, and biasing protrusion 38 in other arrangements. The protrusion 68 can have any desired cross-sectional shape, width, and length. In one example, the protrusion 68 extends across an entire width of the valve flap 34, while in another arrangement the biasing protrusion 68 is a cylindrical shaped member having a rounded distal end.

FIGS. 16F, 17F, 18F illustrate a valve flap 34 that is void of protrusions and connection apertures. The valve flap 34 of FIGS. 16F, 17F, 18F has a generally circular construction and uniform thickness, although many variations of this construction void of protrusions and connection apertures are possible.

Figure 11:
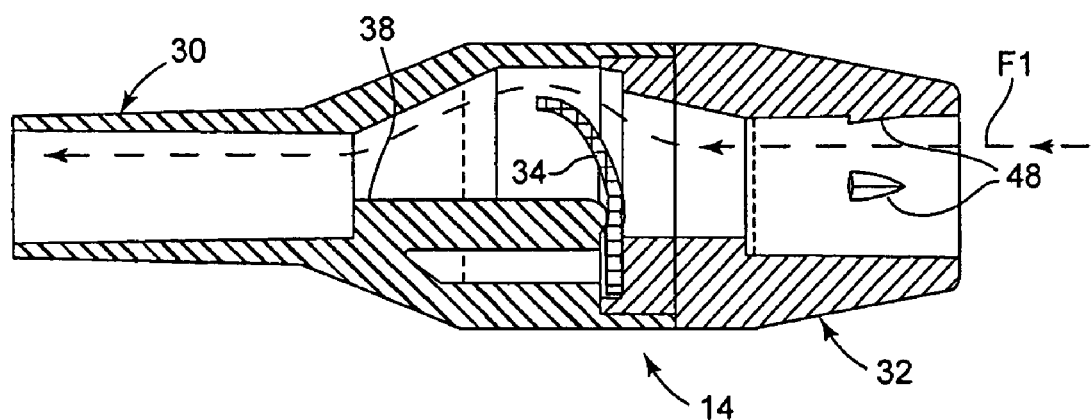
FIG. 11 is a schematic cross-sectional side view of the example backflow device shown in FIG. 10, wherein the valve flap is in an open state.
Figure 20B:
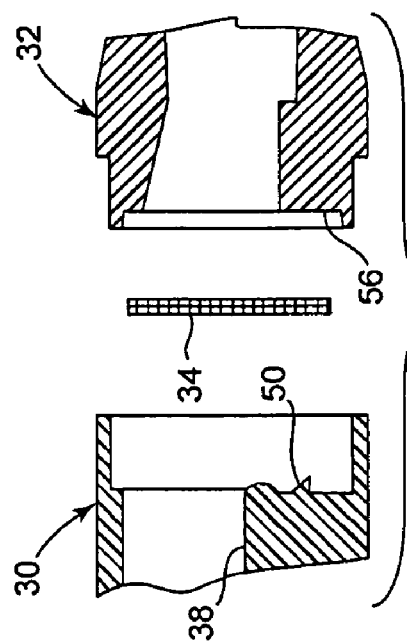
FIG. 20B is a schematic exploded cross-sectional side view of the backflow device shown in FIG. 20A.
Figure 20A:
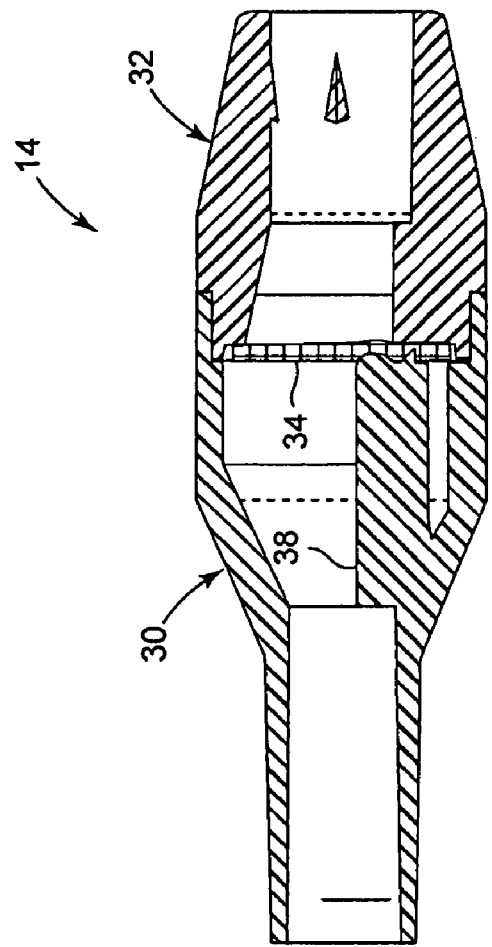
FIG. 20A is a schematic cross-sectional side view of another example backflow device in accordance with the present disclosure, wherein the connection protrusion includes a barb construction.
Figure 23:
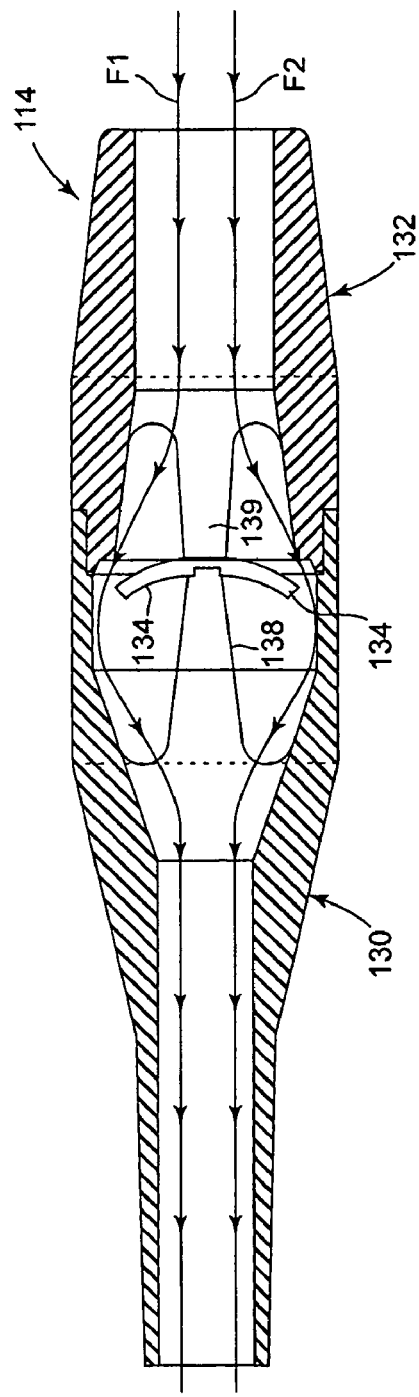
FIG. 23 is a schematic cross-sectional side view showing fluid flow through another example backflow device that includes the valve flap of FIG. 23.

When assembled, the backflow prevention assembly 14 provides for opening and closing of a fluid flow path through the backflow prevention assembly determined by a position of the valve flap 34 relative to the valve seats 56. One or both of the biasing protrusion 38 of the proximal housing portion 30 or the protrusion 68 of the valve flap 34 exerts an axially directed force upon the valve flap 34 that biases the valve flap 34 into the closed position before a threshold vacuum force in the proximal housing portion 30 has been met. When a vacuum pressure condition exists in the proximal housing portion 30 (e.g., upon application of a vacuum force at the flow orifice 46) that exceeds a threshold vacuum pressure condition, the top end portion 62 of the valve flap 34 moves proximally as shown in FIG. 11 to provide an open flow condition in the backflow prevention assembly 14. When in the open position, fluid flows along a flow path F1 as shown in FIG. 23 from the tube orifice 52 in the distal housing portion 32 to the tube orifice 52 in the proximal housing portion 30. When the vacuum pressure condition in the proximal housing portion 30 is reduced from the threshold vacuum pressure condition, the valve flap 34 returns to the closed position shown in FIG. 10 upon the biasing force exerted by the biasing protrusion 38. When in the closed position shown in FIG. 10, the backflow prevention assembly 14 substantially prevents backflow of substances positioned in the suction assembly 10 that are located proximal of the valve flap 34. An example range of threshold vacuum pressure conditions less than about 15 lb/in$^2$ (psi), the atmospheric pressure at sea level. In one example, the threshold pressure condition is in the range of about 6 to about 12 psi. Another way of measuring vacuum pressure is in inches of Mercury (Hg), wherein all values greater than zero inches of Mercury is a vacuum condition (i.e., less than atmospheric pressure). In one example, the threshold vacuum pressure condition is in the range of about 1 to about 20 inches of Mercury, and more preferably about 6 to about 8 inches of Mercury.

The valve flap 34 shown with reference to FIGS. 16B, 17B, 18B includes a bending recess 66 that extends across a width of the valve flap 34 at a location between the top and bottom end portions 62, 64. The valve flap 34 is configured to bend about this bending recess 66 and is held in place between the proximal and distal portions 30, 32 along a bottom portion 64 of the valve flap 34.

Figure 22:
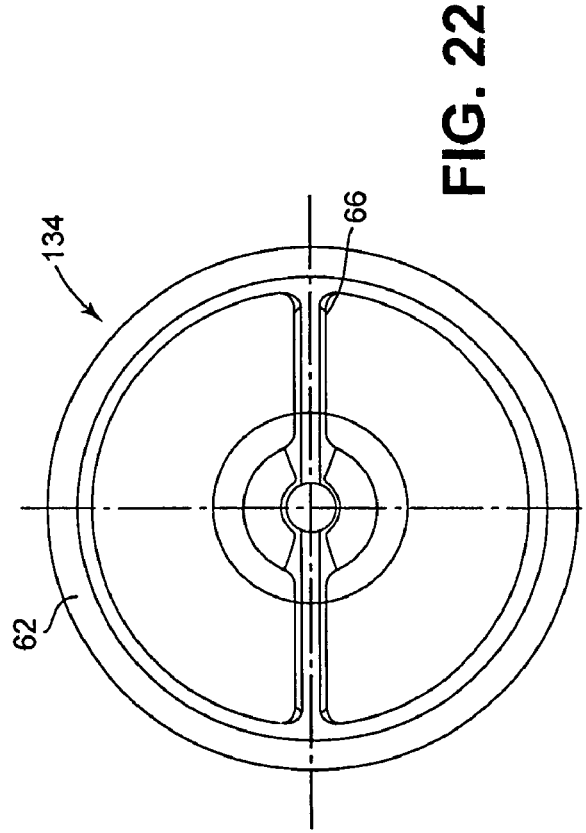
FIG. 22 is a schematic front view of another example valve flap in accordance with the present disclosure, wherein the valve flap is bendable about a lateral centerline.
Figure 31:
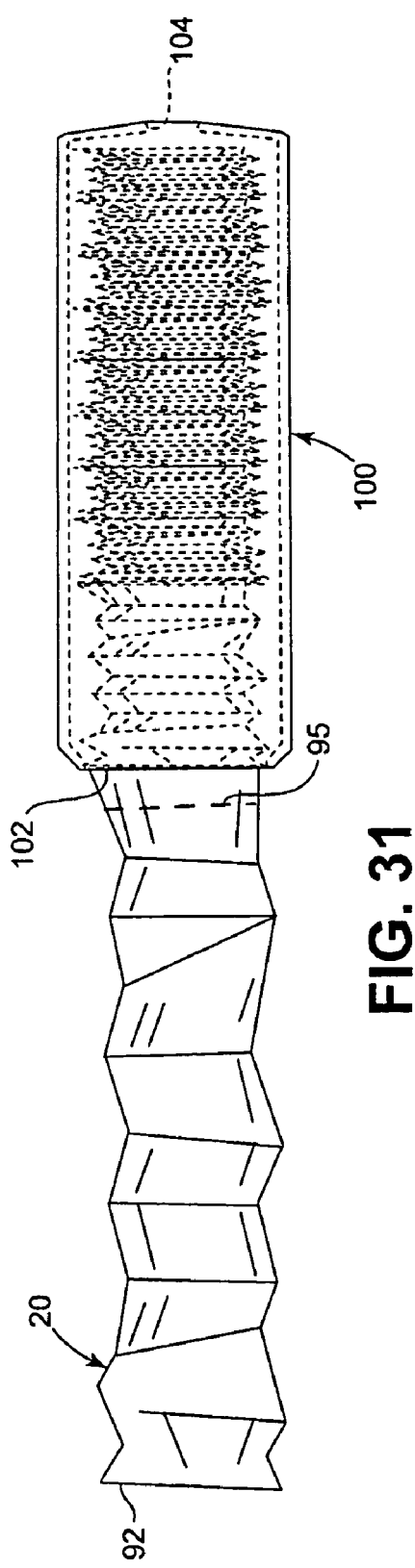
FIG. 31 is a schematic side view of the cover member and housing shown in FIG. 30.

FIGS. 22 and 23 illustrate another example valve flap 134 that includes a bending recess 66. The valve flap 134 is engaged by a modified biasing protrusion 138 that engages the valve flap 134 along the bending recess 66 to help hold the valve flap 134 in a retained position between proximal and distal portions 130, 132 of the backflow prevention assembly 134 (see FIG. 23). FIG. 23 illustrates the valve flap 134 in a bent state within a backflow prevention assembly 114 upon application of a vacuum pressure in the proximal housing portion 130 that exceeds the threshold vacuum condition. The valve flap 134 can bend about bending recess 66. The valve flap 134 can also bend into a conical or concave shape about the biasing protrusion 138. The distal housing portion 132 can include additional structure such as a retention protrusion 139 that helps hold the valve flap 134 at a fixed location. The biasing protrusion 138 and retention protrusion 139 can have shapes and sizes that promote bending of the valve flap 134 into a conical or concave shape, or bending about the bending recess 66. The bent shape of the valve flap 134 can provide an alternate flow path F2 below or around any other peripheral portion of the valve flap 134. The valve flap 134 can also provide for reduced noise and other operational advantages in some instances.

FIGS. 24A-B illustrate another example backflow prevention assembly 214. The backflow prevention assembly 214 proximal and distal portions 230, 232, a biasing protrusion 238, a retention protrusion 239, and a valve flap 234. The biasing protrusion 238 includes a contoured shape (e.g., a convex shape) at its distal end. The retention protrusion 239 includes a shape at its proximal end that mirrors the contoured shape of the biasing protrusion 238 (e.g., a concave shape). The biasing protrusion 238 can also include a connection protrusion 250 that is arranged to engage the valve flap 234 to help retain the valve flap 234 in a predetermined position when the backflow prevention assembly 214 is assembled. The connection protrusion 250 can have a barb-like shape. Alternatively, the connection protrusion 250 can have any desired shape and size that would be helpful in retaining the valve flap 234 in a desired position.

The contoured shapes of the biasing protrusion 238 and retention protrusion 239, as well as the axial position of the engagement point of the protrusions 238, 239 with the valve flap 234 relative the valve seat 56 tend to bias the valve flap 234 in the closed position.

FIGS. 24C-D illustrate another example backflow prevention assembly 314. The backflow prevention assembly 314 proximal and distal portions 330, 332, a biasing protrusion 338, a retention protrusion 339, and a valve flap 334. The biasing protrusion 338 includes a contoured shape (e.g., a concave shape) at its distal end. The retention protrusion 339 includes a shape at its proximal end that mirrors the contoured shape of the biasing protrusion 338 (e.g., a convex shape). The mirrored shapes of the biasing protrusion 338 and retention protrusion 339 help bias the valve flap 334 into a closed position.

The axial position of the engagement point of the protrusions 338, 339 with the valve flap 234 relative the valve seat 56 tend to bias the valve flap 234 in the open position away from valve seat 56. The contoured shapes of the protrusions 338, 339 tend to bias the valve flap 334 into engagement with the valve seat. The axial point of engagement point of the protrusions 338, 339 with the valve flap 234 relative the valve seat 56 can be modified in this and other embodiments (e.g., assembly 214 discussed above) in combination with various shapes and sizes of the protrusions 338, 339 to vary the performance of valve flap 334.

The valve flaps 134, 234, 334 shown in FIGS. 23-24D can be, for example, the valve flap 134 shown in FIG. 22, or any one of the valve flaps 16A-F described above. Other valve flap configurations are possible for use with any of the backflow prevention assemblies described above, include valve flaps that are co-molded or otherwise integrally formed with at least one of the proximal and distal portions (e.g., portions 30, 32) of the backflow prevention assembly.

One advantage related to the valve flaps disclosed with reference to FIGS. 1-24D is that the valve flaps can be manufactured using different manufacturing processes, which could offer simpler and less costly manufacturing process steps for the valve and the overall device. For example, the valve flaps shown in FIGS. 16A and 16B can be merely stamped from a sheet of flexible material rather than being molded as an individual part. The valve flap 34 can also be generated as a separate piece from each of the housing portions 30, 32. As a result, the valve flap 34 can be made from any desired material using any desired process that is not limited in any respect to the manufacturing processes and materials used for the housing portions 30, 32. Preferably, the valve flap comprises a material such as a Silicone or Thermal Plastic Elastomer or other polymeric material. The material selection can be changed to gain different bending responses from the valve flap for different application of the device, and have an effect on properties of, for example, elasticity, stiffness, and moldability. The materials used for the valve flap can also provide a combination of properties that can influence such performance considerations as acoustic vibration.

The ON/OFF valve assembly 16 includes a valve housing 70, a valve member 72, a valve actuator 74, a connection boot 76, a connection orifice 78, and a tube connector 80 (see FIG. 4). The valve actuator 74 is exposed on an exterior of the ON/OFF valve assembly 16 so as to be engaged by a user. The valve actuator 74 moves between a closed orientation shown in FIG. 4 wherein the actuator 74 is positioned at a proximal location and an open position wherein the actuator 74 is moved distally of the valve member 72. Movement of the valve actuator 74 between the proximal and distal positions moves the valve member 72 between a position in which fluid flow through the ON/OFF valve assembly 16 is prohibited, and a position in which the valve member permits fluid flow through the ON/OFF valve assembly 16.

The connection boot 76 is typically removable from the valve housing 70. In some arrangements, the connection boot 76 comprises a rubber or flexible polymeric material that promotes a fluid tight seal with the valve housing 70 and the neck portion 36 of the backflow prevention assembly 14. The structure and material properties of the connection boot 76 also promote relatively easy removal of the connection boot 76 from the valve housing 70, and insertion and removal of the backflow prevention assembly 14 from the connecting orifice 76. Alternative constructions for the connection boot 76 are shown and described in further detail below with reference to FIGS. 25-27D.

The tube connection 80 extends from a proximal end of the valve housing 70. The tube connector is configured to insert into an open end of the vacuum hose 18. A fluid tight connection is provided between the tube connector 80 and the vacuum hose 18. The size of vacuum hose 18 can vary in different applications. For example, the vacuum hose 18 can have an internal diameter (ID) of about 0.125 inches to about 0.5 inches. In another example, the vacuum hose 18 can have an outer diameter (OD) of about 0.25 to about 0.75 inches. Smaller diameter sized vacuum hoses can be referred to as "low volume" vacuum hoses, and larger diameter sized vacuum hoses can be referred to as "high volume" vacuum hoses in some applications. The size of the tube connection 80 and other features of the assembly 10 can be modified for use with any given size of the vacuum hose 18.

The construction of the ON/OFF valve assembly 16 with the valve member 72 positioned generally centrally between the proximal and distal ends of the valve housing 70 makes it possible for there to be suctioned materials lingering within the connection boot 76, portions of the valve housing 70 that are distal of the valve member 72, and ejector tube assembly 12 that are retained there after the valve member 72 is turned to an OFF position. Thus, when the ejector tube assembly 12 and/or backflow prevention assembly 14 is replaced between uses for different patients, there is potential for those retained substances to backflow into the ejector tube assembly 12 and out of the ejector tip 28 before the valve member 72 is again opened to suction those substances out of the suction assembly 10.

When the assembly 10 is in use drawing substances (e.g., fluid) through the assembly under a vacuum pressure applied via the vacuum hose 18, the vacuum pressure can be reduced if the inlet to the ejector tip 28 (see FIG. 3) is blocked. The ejector tip 28 can be blocked when, for example, the ejector tip 28 engages a sealing surface such as a patient's flesh at the suctioning site or an air impervious material (e.g., plastic sheet). When the ejector tip 28 is blocked, the pressure inside assembly 10 is reduced, making it possible for substances in the assembly 10 to flow under gravity forces in the distal direction towards the ejector tip 28. In some limited circumstances, backflow of the substances out of the assembly 10 can occur. The use of the backflow prevention assembly 14 reduces occurrences of such backflow out of the ejector tip 28.

The cover member 20 includes an outer diameter D3, an extended length L2 (see FIG. 8A), an opening restricting member 90, a distal end 92, and a proximal end 94 (see FIGS. 1-4). The cover member 20 is particularly useful for covering at least a portion of the ejector tube assembly 12, at least portions of the backflow prevention assembly 14, and at least portions of the ON/OFF valve assembly 16. In some arrangements, such as the one shown in FIG. 1, the cover member 20 extends from the ejector tube assembly to cover at least a portion of the vacuum hose 18. The cover member 20 can be constructed of a material that is collapsible upon itself such as into the collapsed position shown in FIG. 2, and then able to re-extend into the extended position shown in FIG. 1.

Figure 6:
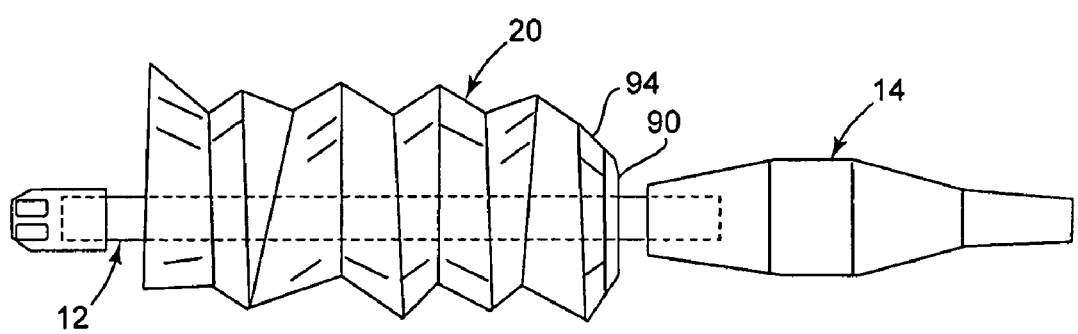
FIG. 6 is a schematic side view of the example assembly shown in FIG. 5, wherein the cover includes a sealed end near the backflow device.
Figure 10:
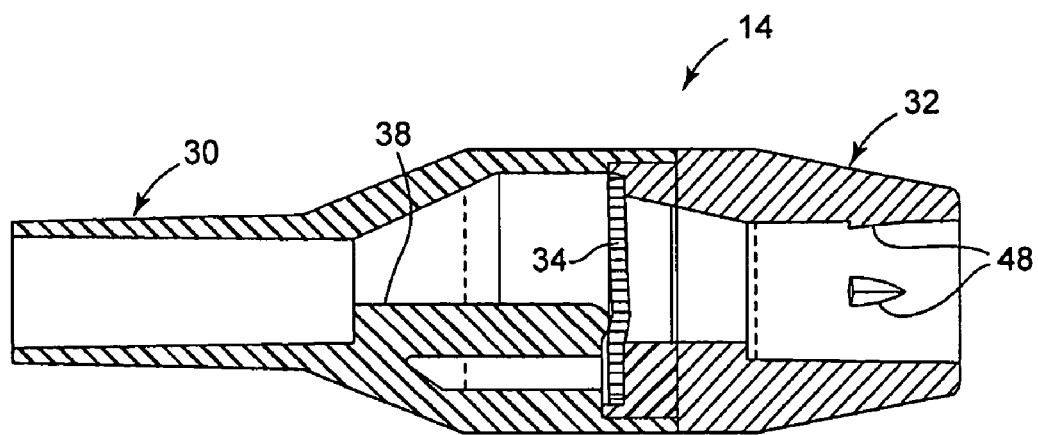
FIG. 10 is a schematic cross-sectional side view of an example backflow device in accordance with the present disclosure, wherein the valve flap is in a closed state.

The opening restricting member 90 can be positioned at the distal end 92 as shown in FIGS. 1-4 to help restrict the size of the distal opening of the cover member 20. Preferably, the opening restricting member 90 helps retain the cover member 20 on the ejector tube 22 without permitting proximal retraction over the backflow prevention assembly 14 and/or the ON/OFF valve assembly 16. The opening restricting member 90 can also provide a limited opening size that prevents distal advancement of the distal end of the cover member 20 beyond the ejector tip 28. In other arrangements, the opening restricting member 90 can be positioned at the proximal end opening of the cover member as shown in FIG. 6. In still further example arrangements, an opening restricting member 90 can be positioned along the length of the cover member 20 at a location between the proximal and distal ends. In other arrangements, multiple opening restricting members 90 can be used at various locations along the length or at proximal and distal ends of the cover member 20. The opening restricting member 90 can comprise an elastic material such as, for example, polyethylene, polyester, latex, or other material such as polyvinyl chloride. In other arrangements, the restricting member 90 is merely a reduced diameter portion of the cover member created by, for example, heat sealing. The opening restricting member 90 can be adjustable in size and shape, or be fixed is size. In one arrangement, the size of the opening restricting member 90 is fixed in size unless permanently deformed by application of a radially outward directed force.

The cover member 20 can comprise a length of tubular structured material. The tubular structure can be generated using an extrusion process, or it can be constructed using a sheet of material that is rolled across its width with side edges sealed together to form the tube shaped structure. The cover member 20 can include a corrugated structure along at least a portion of its length that promotes retracting and extending of the cover member 20 as needed along its entire length to cover certain features of the suction assembly 10, or to provide elongation of the cover member 20 at certain features of the suction assembly 10 such as the ON/OFF valve actuator 74. FIG. 9 illustrates a continuous roll 98 of cover member material. Predefined lengths of the cover member 20 can be indicated by perforations 95, wherein the distance between the distal end 92 and the perforation 95 is in the range of the length L2 shown in FIG. 8A. The length L2 can be in the range of about 8 to about 24 centimeters, and more preferably about 16 to about 22 centimeters. Another means for collecting a continuous length of cover member is described below with reference to FIGS. 34-37.

The cover member 20 can include, in addition to or in place of the opening restricting member 90, a length restricting member 96 that extends along at least a portion of the length L2. FIG. 8B illustrates a single length restricting member 96 extending from the distal end 92 to the proximal end 94 of the cover member 20. FIG. 8C illustrates two separate lengths restricting members 96A, 96B extending between the distal and proximal ends 92, 94. In some arrangements, the length restricting member 96 comprises an elastic material such as, for example, polyethylene, polyester, latex or other plastic materials commonly used polymeric material. In other examples, the length restricting member 96 functions as a stiffening member that maintains a predefined shape that is applied by the user or corresponds to the shape of other features of the suction assembly 10. In still further arrangements, the length restricting member 96 can be replaced with a length extending member that promotes extension of the cover member 20 to its maximum length and resists bunching or restricting of the cover member 20 along its length (e.g., the restricted arrangement shown in FIG. 2).

The length restricting members 96A, 96B can be separate members that extend along the length L2, or can be a continuous member that extends around an entire outer periphery of the cover member 20. In still further arrangements, the members 96A, 96B can replace portions of the cover member 20. The opening restricting member 90 and length restricting members 96 can be secured to the cover member 20 in a separate manufacturing step, can be co-molded or co-extruded with the cover member 20, or attached in any way desired, for example, an end user.

In the application of a dental or medical environment, a primary advantage of the cover member 20 is to permit the user to operate the ON/OFF valve 16 without having to remove their gloves and while maintaining sanitary conditions. Currently, users working with a medical or dental patient wear gloves to promote sanitation. The user often operates the uncovered and possibly contaminated ON/OFF valve without taking off their gloves. In some cases some users will go through the trouble of removing their gloves after touching a contaminated ON/OFF valve. If the gloves are removed, then it takes time to take them off and put back on a new pair. In some cases, the gloves are wet and sticking and a new pair is required to continue working on the patient.

The Example Connection Boots of FIGS. 25-28D

The connection boot 76 used with the ON/OFF assembly 16 can be modified to include a backflow prevention valve for use in addition to or in place of the backflow prevention assembly 14 described above with reference to FIGS. 1-25. FIG. 27 illustrates an example boot valve assembly 82 shown assembled with an ejector tube assembly 12. The boot valve assembly 82 includes an adapter 84 and a valve member 86. The adapter 84 includes a connecting orifice 78, a plurality of barb members 48 extending into the connecting orifice 78, and a proximal end surface that defines a valve seat 85. (See FIG. 28.) The barbs 48 help retain the proximal end of the ejector tube 22 within the adapter 84. The valve seat 85 provides a stop surface that defines a distal most axial position of the valve member 86 when in the closed position. The valve member 86 extends from an internal sidewall of the connection boot 76.

The examples shown in FIGS. 25-28C include a valve member that is integral with a sidewall of the connection boot 76. FIGS. 25A, 26A show the valve member 86 biased in the distal direction before assembly. When assembled, the adapter 84 in the example of FIG. 25 and the ejector tube assembly 12 in the example of FIG. 26 move the valve member 86 into a closed position, whereby the valve member 86 imposes a biasing force in the distal direction. This distally directed biasing force prevents the valve member 86 from moving proximally into an open position until a threshold vacuum pressure condition is exceeded.

Variations of the boot valve assembly 82 shown in FIGS. 25 and 26 are included in FIGS. 27A-C and 28A-C. In each of these examples, the connection boot 76 is configured such that the adapter 84 is not needed. The proximal end of the ejector tube 22 can be secured directly to the connecting orifice 78 of the connection boot 76. In FIGS. 27A-B, the valve member 86 is positioned at a proximal end of the connecting orifice 78 so as to be positioned directly adjacent to the proximal most end of the ejector tube 22 when the ejector tube 22 is inserted in the connecting orifice 78. FIG. 27C includes a valve member 86 that is positioned spaced proximal of the connecting orifice 78 so as to be functionally closer to the valve housing of the ON/OFF valve assembly.

FIGS. 27D, 28D illustrates a further example in which a removable valve assembly 88 is positioned within the connection boot 76. The removable valve assembly 88 includes first and second portions 87, 89 with the valve member 86 captured there between. The outer dimensions of the removable valve assembly 88 match the internal dimensions of the connection boot 76 thereby helping maintain the removable valve assembly 88 in a desired axial position within the connection boot 76. The valve seats and related structure of the removable valve assembly 88 is similar in some respects to features of the backflow prevention assembly housing portions and valve flap described above with reference to FIGS. 10-24D.

Any of the arrangements discussed above with reference to the attached figures that include an ejector tube can be constructed as a single piece object. For example, the combination of the ejector tube assembly 12 with the backflow prevention device 14 shown in FIGS. 1-4 can include a combined, single piece construction of the ejector tube assembly 10 with the distal housing portion 32 or another portion of the backflow prevention device 14. In another example, the ejector tube assembly 12 shown in FIGS. 25 and 26 can be formed as a single piece with the connection boot 76, adapter 84, or a different distal portion of the ON/OFF valve assembly 16.

Additional Cover Member Examples of FIGS. 29-33

The example cover members described herein can be used in combination with various features of the suction assembly 10 individually or in subassemblies. For example, the cover member 20 can be used in a subassembly with the ejector tube assembly 12. FIG. 7 illustrates such a subassembly. In the subassembly of FIG. 7, the opening restriction member 90 helps retain the cover member 20 along the length of the ejector tube 22. The proximal end of the ejector tube 22 can be secured directly to the connection boot 76 of the ON/OFF valve assembly 16 as shown in FIG. 29. The cover member 20 can be extended to cover at least a portion of the ejector tube 22 and substantially all of the ON/OFF valve assembly 16. Portions of the cover member 20 can also extend proximally beyond the ON/OFF valve assembly 16 to cover at least portions of the vacuum hose 18.

Figure 5:
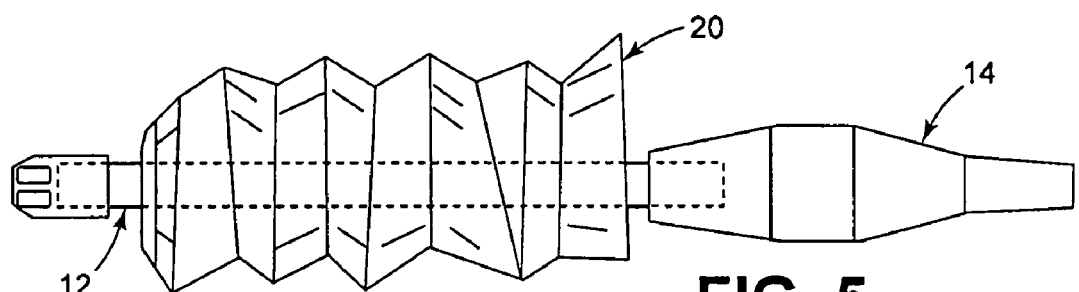
FIG. 5 is a schematic side view of an example assembly in accordance with the present disclosure that includes an ejector tube, backflow device and cover, wherein the cover includes a sealed end near the ejector tip.

In another example arrangement, the cover member is provided with a subassembly that includes the ejector tube assembly 12 and the backflow prevention assembly 14 as shown in FIGS. 5 and 6. The proximal end of the ejector tube 22 is secured directly to the distal end of the backflow prevention assembly 14 (see also FIGS. 1-4). In this arrangement, the opening restrictor member 90 helps retain either the distal or the proximal end of the cover member 20 along the length of the ejector tube 22 between the ejector tube 28 and the backflow prevention assembly 14.

Subassemblies of the cover member with the ejector tube assembly and/or the backflow prevention assembly can be provided as disposable parts that are easily replaceable when used with the ON/OFF valve assembly 16. The cover member 20 provides a physical boundary between the user and the ON/OFF valve assembly 16 and/or the backflow prevention assembly 14, which may have been touched or exposed to unsanitary conditions between uses of the suction assembly 10 on different patients. A primary purpose of the cover member 20 is to provide a barrier that will become contaminated when used. The cover member 20 captures unsanitized portions of the suction assembly 10 within the interior of the cover and provides a sanitary surface on the exterior of the cover. The cover prevents the user of the ON/OFF valve assembly 16 from coming in contact with the surface of the ON/OFF valve assembly 16, which may be contaminated. The cover member 20 also inhibits transfer of contaminates on the user's hands or gloves to the ON/OFF valve assembly 16 and other features within the interior of the cover member 20. The cover member 20 may become contaminated with fluids, bacteria and other contaminates associated with the patient during use of the suction assembly 10. Each time the cover member 20 is removed from the suction assembly 10, those contaminates that have been transferred to the exterior or interior of the cover member 20 are removed with the cover member 20, and therefore removed from possible transfer to the next patient by way of the user.

Now referring to FIGS. 30-33, an alternative cover member configuration and retention structure is now described. FIG. 30 illustrates a cover member housing 100 that retains within it a continuous length of cover member 20 that is restricted into a contracted state. The cover member housing 100 includes distal and proximal openings 102, 104. The proximal opening 104 is sized to extend the vacuum hose 18 through an interior of the cover member housing 100 and into engagement with the tube connector 80 of the ON/OFF valve assembly 16. The cover member housing 100 includes an internal dimension 108 that can be at least as great as a maximum diameter D3 of the cover member 20. The distal opening 102 is shown in FIGS. 30-33 being about the same as dimension D3 of the cover member 20. In other arrangements, the distal opening 102 can have a smaller size and can be as small as the outer diameter of the vacuum hose 18 plus two times the thickness of the cover member material in order to permit removal of the cover member 20 from between the vacuum hose 18 and opening 102.

The cover member housing 100 is shown in FIG. 30 positioned completely proximal of the proximal end of ON/OFF valve assembly 16. In other arrangements, the cover member housing 100 can be positioned distally so at least a portion of the ON/OFF valve assembly 16 is positioned internal of the cover member housing 100.

Figure 33:
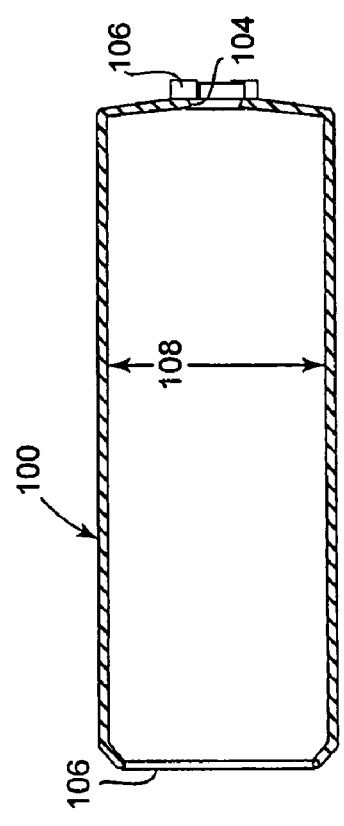
FIG. 33 is a schematic cross-sectional side view of another example side member housing in accordance with the present disclosure, the side member housing including a fastener member to hold a position of the side member housing member relative to the ON/OFF valve.

The cover member housing 100 can further include a connector 106 at either the distal or proximal opening 102, 104. FIG. 33 illustrates the connector 106 adjacent the proximal opening 104. The connector 106 can be used to secure the cover member housing 100 to the vacuum hose 18 at a predefined location along the length of the vacuum hose 18. In other arrangements, the connector 106 can be used to secure the cover member housing 100 to other features such as, for example, the ON/OFF valve housing 70 or other features of the suction assembly 10.

The cover member housing 100 can further include a cutting member (not shown) positioned at, for example, a location adjacent the distal opening 102 to help in cutting off a length of the cover member 20 that has been drawn distally out from the cover member housing 100. As mentioned above, the cover member 20 can include perforations 95 at positions along its length to assist in removing a desired amount of the cover member length that has been drawn distally out of the cover member housing 100. In some arrangements, the cover member 20 can include an opening restricting member 90 positioned on at least one of a proximal and distal side of the perforations 95 to provide restriction of one or both ends of the cover member 20 that has been drawn out of the cover member housing 100.

Figure 32:
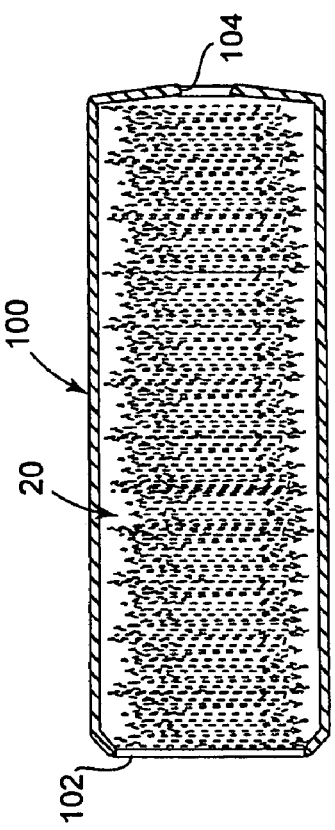
FIG. 32 is a schematic cross-sectional side view of the side member and housing shown in FIG. 31, wherein the cover member is completely retained in the housing.

FIG. 32 illustrates a continuous length of cover member 20 compressed within the cover member housing 100. The continuous length of cover member 20 supplied to the housing 100 can be supplied from, for example, the roll 98 of cover member 20 shown in FIG. 9. The cover member housing can be provided with enough length of cover member 20 for a predetermined number of lengths L2 of cover member. The predetermined number of lengths L2 can be, for example, the number needed for a certain number of uses of the suction assembly 10 for a given number of patients in a certain time frame. For example, the housing 100 can hold the number of lengths L2 of cover member 20 for use in a half day, full day, week, or month's worth of patients being treated. The total length of cover member 20 compressed within an particular configuration of the cover member housing 100 can vary depending on, for example, the material diameter (D3), whether or not opening restricting members or length restricting members are used with the cover member 20, and other considerations related to the construction of the cover member 20. The amount of cover member material held within the cover member housing 100 is also dependent upon, for example, the internal dimensions including, for example, the internal diameter and internal length of the cover member housing 100.

In some arrangements, the cover member housing 100 can be permanently attached to the vacuum line. The cover member housing can be loaded with refill cartridges or refill lengths of the cover tubing as desired in any of the above described arrangements. The cover member housing 100 can also be constructed as a two piece design that can be disassembled in part to refill the housing and then re-assembled for use.

Additional Backflow Device Examples of FIGS. 34-43

Figure 34:
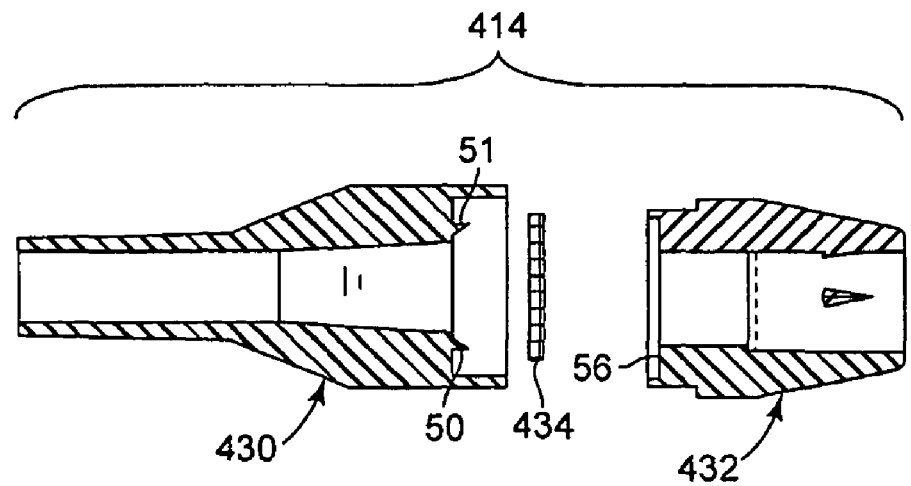
FIG. 34 is a schematic exploded cross-sectional side view of another example backflow device in accordance with the present disclosure, wherein the valve flap is retained by a pair of oppositely arranged barbs.
Figure 35:
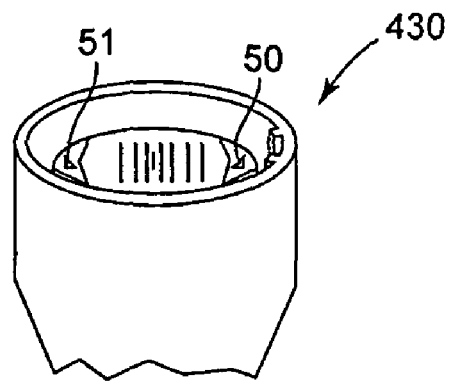
FIG. 35 is a schematic perspective view of a distal housing portion of the backflow device shown in FIG. 34.
Figure 36:
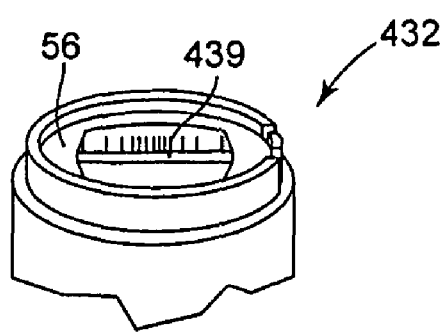
FIG. 36 is a schematic perspective view of a proximal housing portion of the backflow device shown in FIG. 34.

FIGS. 34-36 illustrate another example backflow prevention assembly 414. The backflow prevention assembly 414 includes proximal and distal portions 430, 432, a valve flap 434, and a retention protrusion 439. The proximal portion 430 includes a pair of connection protrusions 50, 51 that extend towards and engage the valve flap 434 when the assembly 414 is assembled. The connection protrusions 50, 51 can be shaped with a pointed tip that engages the valve flap 434 to help retain the valve flap 434 in a predetermined rotated position. The connection protrusions 50, 51 are typically arranged opposite each other (e.g. at 180° rotated positions relative to each other). The portions of the valve flap 434 that are not engaged by the connection protrusions 50, 51 are movable relative to the valve seat 56 to create an airflow path from the distal portion 432 to the proximal portion 430.

The distal portion 432 can include a protrusion 439 that engages the valve flap 434. The protrusion 439 can be arranged extending along a line between the connection protrusions 50, 51. The protrusion 439 can help stabilize the valve flap 434 when the valve flap 434 is in an open orientation in which portions of the valve flap 434 move away from the valve seat 56 to create the fluid flow path between proximal and distal portions 430, 432.

Figure 37:
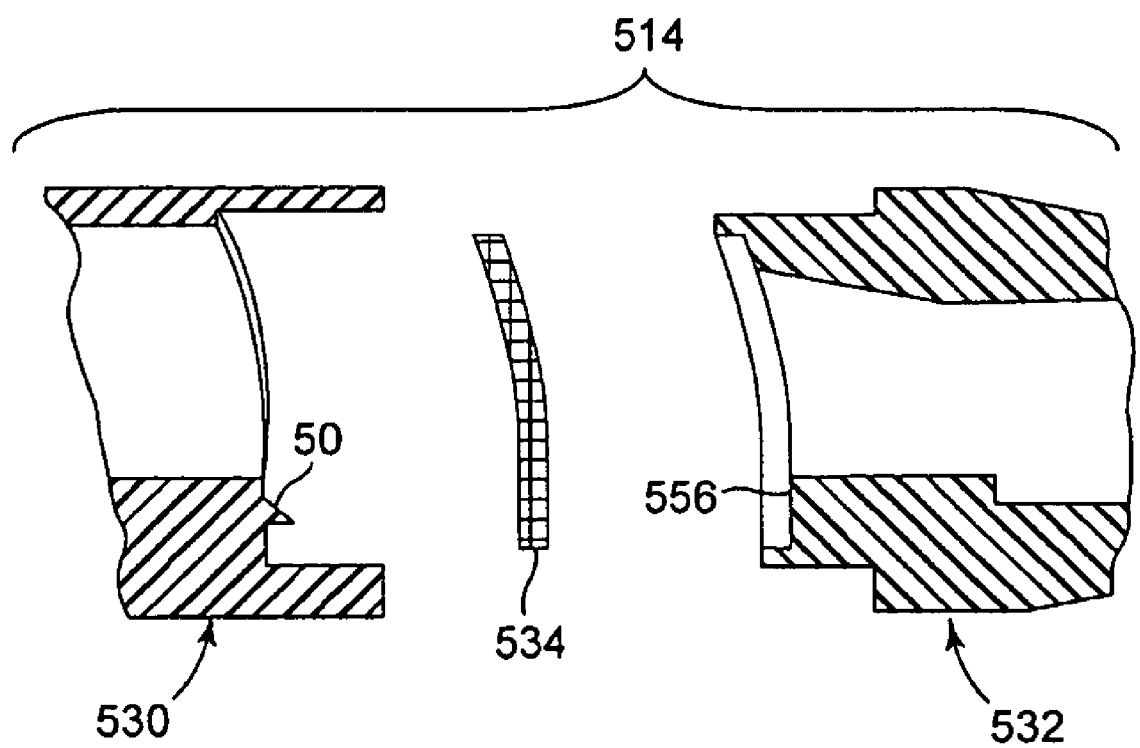
FIG. 37 is a schematic exploded cross-sectional side view of another example backflow device in accordance with the present disclosure, wherein the distal and proximal housing portions define an arch shaped valve seat.

FIG. 37 illustrates another example backflow prevention assembly 514. The backflow prevention assembly 514 includes proximal and distal portions 530, 532, a valve flap 534. The proximal portion 530 includes a connection protrusion 50 arranged to engage the valve flap 534 when the assembly 514 is assembled. The distal portion 532 includes an arc shaped valve seat 556. The valve seat 556 is constructed to bias the valve flap 534 into a bent orientation relative to the generally planar orientation that the valve flap 534 typically maintains when in a rest state. The bent orientation of the valve flap 534 resulting from the arc shape of the valve seat 556 tends to create a biasing force within the valve flap 534 as the valve flap 534 attempts to return to the planar orientation that helps maintain contact of the valve flap 534 in a closed state against the valve seat 556. The bend formed in the valve flap 534 by the valve seat 556 can help return the valve flap 534 into a closed orientation after a vacuum pressure condition that moves the valve flap 534 into an open orientation is released.

Portions of the proximal portion 530 can also be formed with an arch shape. In one arrangement, the arc shape formed in the proximal portion 530 generally mirrors the arc shape of the valve seat 556.

Figure 38:
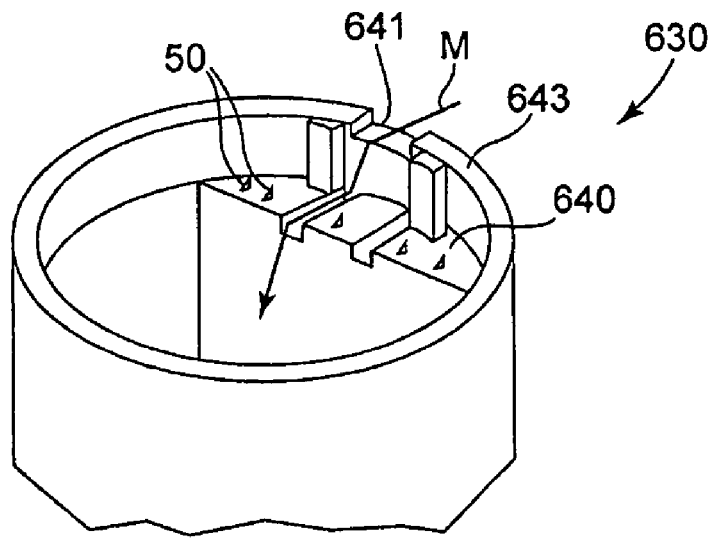
FIG. 38 is a schematic perspective view of a housing portion of another example backflow device, wherein the housing portion defines an air inlet port.

FIG. 38 illustrates another example proximal portion 630 for use with the backflow prevention assemblies described herein. The proximal portion 630 includes a plurality of connection protrusions 50 positioned along a mating surface 640. The connection protrusions 50 are arranged and configured to engage a valve flap of a backflow prevention assembly. A vacuum control air inlet port 641 defined in the proximal portion 630 defines an air inlet flow path M. A portion of the vacuum control air inlet port 641 is defined in a distal surface 643 and another portion is defined in the mating surface 640.

The flow path M provides air flow from external the proximal portion 630 to internal the proximal portion 630. The vacuum control air inlet port 641 permits air to bypass the valve flap of the backflow prevention assembly until a high enough vacuum pressure condition is generated within the backflow prevention assembly to move the valve flap to an open orientation. Controlling the shape and size of the vacuum control air inlet port 641 can help maintain the valve flap in the closed orientation until a specific amount of vacuum pressure is achieved in the backflow prevention assembly.

Figure 39:
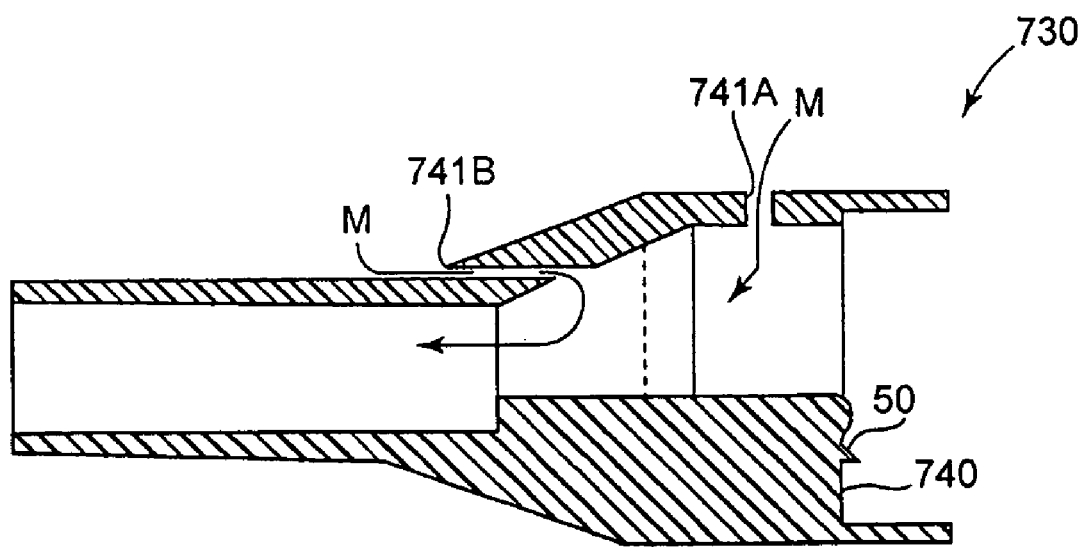
FIG. 39 is a schematic cross-sectional side view of a housing portion of another example backflow device, wherein the housing portion defines a plurality of air inlet ports.

FIG. 39 illustrates another example proximal portion 730 for use with the backflow prevention assemblies described herein. The proximal portion 730 includes vacuum control air inlet ports 741A, 741B that each define an air inlet flow path M. The vacuum control air inlet ports 741A, 741B permit air to bypass the valve flap of the backflow prevention assembly similar to the port 641 described above. The vacuum control air inlet ports 741A, 741B are defined in the proximal portion 730 at a location proximal of a mating surface 740.

Figure 40:
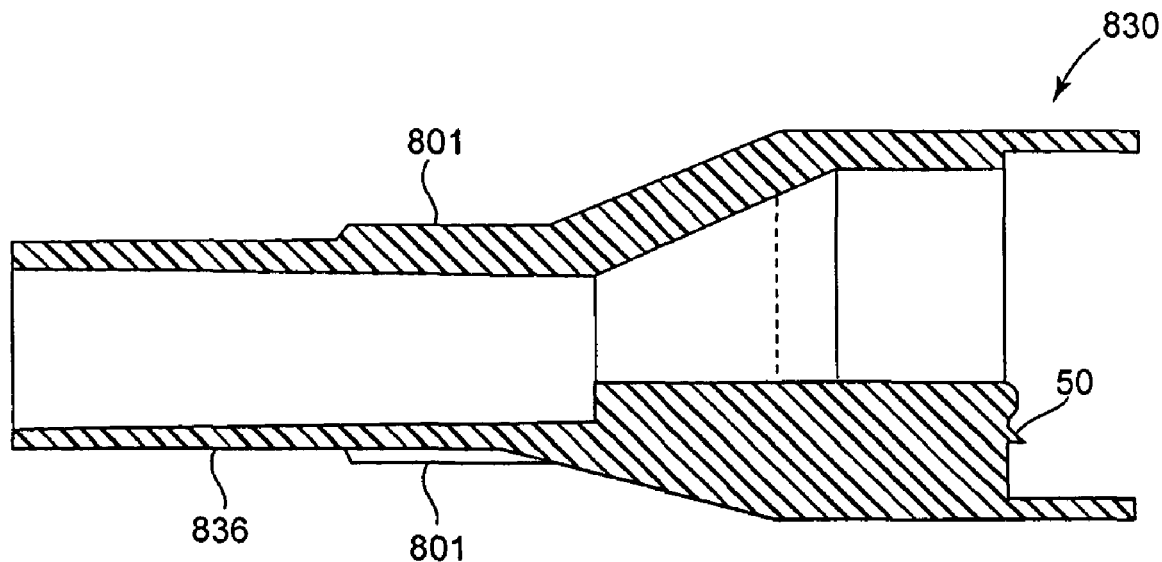
FIG. 40 is a schematic cross-sectional side view of a housing portion of another example backflow device, wherein the housing portion includes a plurality of external contact rib members.
Figure 41:
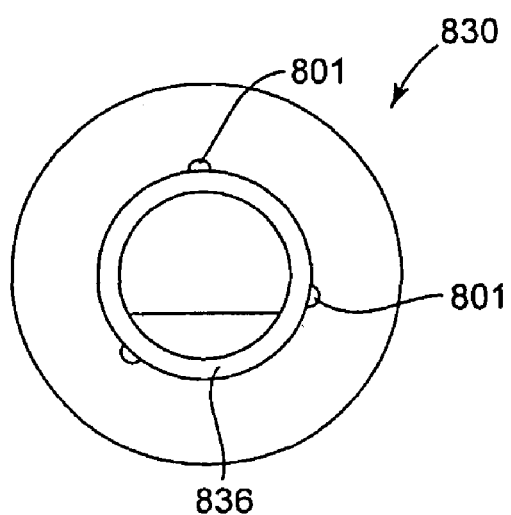
FIG. 41 is a schematic end view of the housing portion shown in FIG. 40.

FIGS. 40-41 illustrate another example proximal portion 830 for use with the backflow prevention assemblies described herein. The proximal portion 830 includes a plurality of engagement ribs 801 positioned along an outer surface of a neck portion 836. The ribs 801 can improve engagement between the neck portion 836 and a suction device to which the proximal portion 830 is mounted. Some example structures of a suction device to which the proximal portion 830 could be mounted include a rubber boot and a metal valve housing that includes an internal O-ring. The structure of a suction device to which the proximal portion 830 is mounted can be susceptible to wear over time that results in a loose connection with the proximal portion 830. The engagement ribs 801 can be constructed and arranged to provide positive engagement between the proximal portion 830 and the mounting structure of the suction device before and after such wear occurs.

In some embodiments, the engagement ribs 801 can comprise material that is deformable to permit the ribs 801 to be shaped to whatever size is needed to maintain positive engagement with the mounting structure of the suction device regardless of the amount of wear in the mounting structure. The engagement ribs 801 can have a generally linear shape that extends parallel with a longitudinal axis of the proximal portion 830. Alternatively, the engagement ribs 801 can include contoured portions and portions that wrap around an exterior of the rib portion 836 such as in a helical orientation that is not parallel with the longitudinal axis of the proximal portion 830. Further, there can be any number of engagement ribs 801 provided on the neck portion 836.

Figure 42:
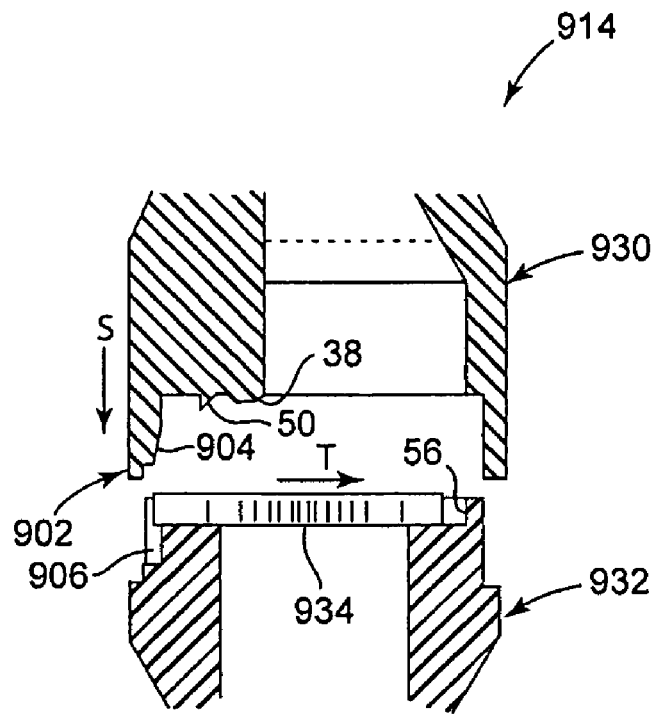
FIG. 42 is a schematic exploded cross-sectional side view of another example backflow device in accordance with the present disclosure, wherein the features of the housing portions assist in orienting the valve flap relative to the housing portions.
Figure 43:
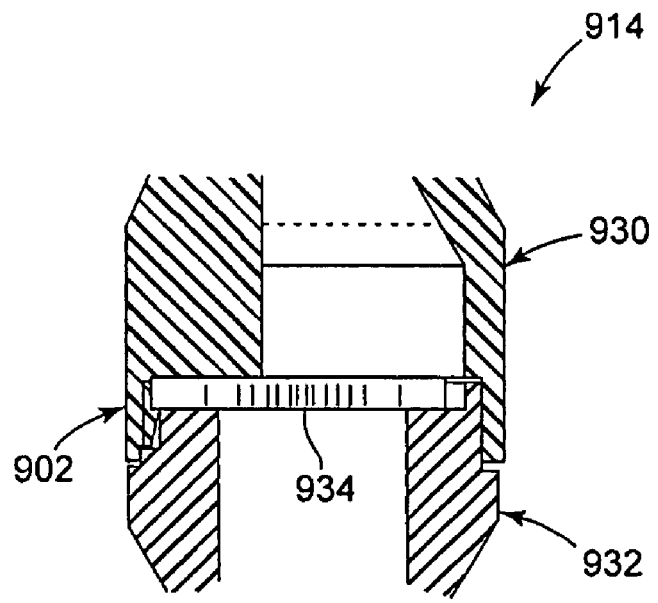
FIG. 43 is a schematic cross-sectional side view of the backflow device shown in FIG. 42.

FIGS. 42-43 illustrate another example backflow prevention assembly 914. The backflow prevention assembly 914 includes proximal and distal portions 930, 932, and a valve flap 934. The proximal portion 930 includes a connection protrusion 50, a biasing protrusion 38, and a key member 902. The key member 902 includes a tapered surface 904 that is constructed to help align the key member 902 with a key slot 906 defined in the distal portion 932.

Typically, the backflow prevention assembly 914 is assembled by positioning the valve flap 934 in a valve seat 56 of the distal portion 930. The valve seat can be sized greater than the maximum dimension of the valve flap 934 such that the valve flap 934 can be misaligned in the valve seat 56. Providing the valve seat 56 with a greater size than the valve flap 934 can make it easier to position the valve flap in the valve seat. The action of inserting the key member 902 into the key slot 906 in the direction S can move the valve flap 934 into proper orientation in the direction T (see FIG. 42). The tapered surface 904 of the key member 902 can help the key member 902 be inserted into the key slot 906 with greater ease. The tapered surface 904 can also provide an engagement surface against which an edge of the valve flap 934 engages after the key member 902 begins to be inserted into the key slot 906 to help move the valve flap 934 in the direction T into a proper orientation relative to the proximal and distal portions 930, 932.

The key features 902, 904, 906 can be combined with any other backflow prevention assembly features described herein.

The Example Valve Flap Configurations of FIGS. 44-68

Some valve flap used in the backflow prevention assemblies can include additional structure that increases resistance to bending in the valve flap. Resistance to bending is sometimes characterized in terms of stiffness. Valve flaps with increased stiffness can be less susceptible to rapid oscillations (e.g., fluttering) in which portions of the valve flap move away from and back into contact with the valve seat. Fluttering can result in an undesirable source of noise when using the backflow prevention assembly. Fluttering of the valve flap can be particularly active when the vacuum pressure condition is maintained within a certain range of the threshold pressure condition needed to move the valve flap into the open state away from the valve seat. Some aspects of the valve flaps described herein, particularly those valve flaps described with reference to FIGS. 44-68 can help reduce noise produced by fluttering.

Stiffness typically defined as the resistance of an elastic body to deflection or deformation by an applied force. The stiffness, k, of a body is $$k=P/\delta$$

where
P is the applied force
$\delta$ is the deflected distance

In the International System of Units, stiffness is typically measured in newtons per meter. The inverse of stiffness is compliance, typically measured in units of meters per newton.

A body may also have a rotational stiffness, k, given by $$k=M/\theta$$

where
M is the applied moment
$\theta$ is the rotation

In the SI system, rotational stiffness is typically measured in newton-meters per radian.

Figure 44:
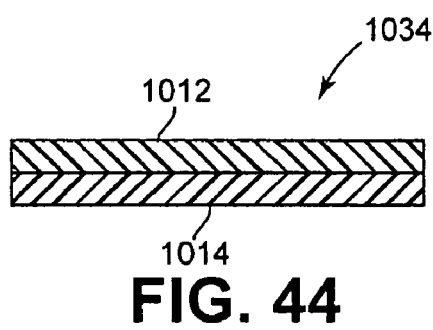

FIG. 44 illustrates an example valve flap 1034 that includes at least two layers 1012, 1014. The layers 1012, 1014 can be separately formed and secured to each other using a bonding method such as, for example, adhesive bonding or heat bonding. Alternatively, one of the layers 1012, 1014 can be formed on the other layer using, for example, using co-molding processes, vapor deposition, and other methods of applying a material layer.

The use of two layers 1012, 1014 can influence bending characteristics of the valve flap as compared to a valve flap that has only a single layer. For example, the use of two layers 1012, 1014 can increase stiffness (i.e., greater resistance to bending) because of, for example, increased total thickness of the valve flap, the addition of bonding material that is used to secure the two layers 1012, 1014 together or the bond structure itself at the interface of layers 1012, 1014, additional friction that is present at the interface of the layers 1012, 1014, or a difference is size, shape, or material composition of one of the layers compared to the other layer.

While the layers 1012, 1014 are illustrated as having generally planar surfaces and uniform thicknesses, various aspects of either of the layers 1012, 1014 can be altered to change bending properties of specific portions of either of layers 1012, 1014 thereby influencing bending properties of the valve flap as a whole.

In some arrangements, the layers 1012, 1014 can be arranged to freely move relative to each other. Alternatively, the layers 1012, 1014 can be secured at every location in which the layers 1012, 1014 interface. The layers 1012, 1014 can also be secured to each other at only predetermined locations that are less than the entire mating surfaces where the two layers engage.

Figure 45:
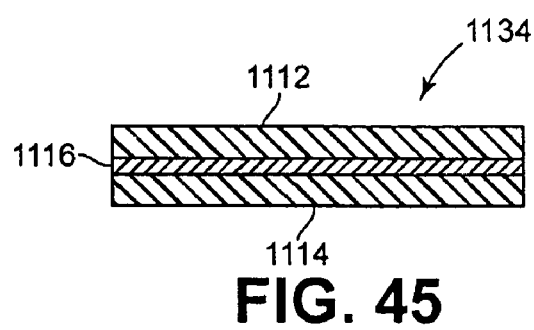

FIG. 45 illustrates another example valve flap 1134 that includes at least three layers 1112, 1114, 1116. The use of three or more layers in the valve flap can influence bending characteristics of the valve flap for at those reasons discussed above concerning the use of two layers. The use of three or more layers can increase the options for customizing the bending characteristics of the valve flap because one of the layers can be provided with any desired feature (e.g., shape, size, material composition) that alone or in combination with features of the other layers can influence bending characteristics of the valve flap. For example, any one of the layers 1112, 1114, 1116 can have a different material composition, shape or size as compared to the other layers. In one example, the middle layer 1116 comprises a material or a construction that is more or less stiff than the layers 1112, 1114 or more or less flexible than the layers 1112, 1114.

Any layer or portion of a layer that influences resistance to bending of the valve flap can be considered a stiffening member or stiffening layer. The stiffening member can comprise various characteristics such as, for example, being degradable over cycles of use, chemically reactive to change colors or other characteristics over cycles of use, or change temperature, shape or size with cycles of use. Some types of stiffening members or stiffening layers can reduce resistance to bending in at least a portion of the valve flap as compared to a valve flap that does not include such a stiffening feature. In the example two-layer valve flap 1034 described above, the mere inclusion of a second layer of material, even if the second layer is the same shape and size and has the same material composition as the other layers and the total valve flap dimensions are the same as a single layer valve flap, the valve flap 1034 can have increased stiffness or less flexibility than the single layer valve flap.

In one example, the stiffening member comprises a paper composition that decomposes to provide decreased stiffening properties after a predetermined number of uses. In another example, the stiffening layer can include a material that changes color after a certain number of uses. In such an example, the change in color results from a chemical reaction could be made to take place at the outlet side of the backflow prevention assembly so that the patient is not exposed to the chemical reaction. In a further example, the stiffening member can comprise a metallic material, a conductive material, an electroactive polymer material (EAP) which when used with other features of the valve flap can perform at least a stiffening function and possible provide other functionality. Such aspects of the stiffening material can be applied to any of the stiffening layers, materials, and valve flap constructions described herein.

Figure 46:
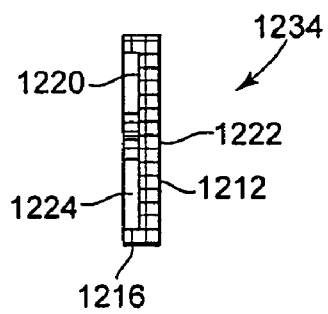

Referring now to FIG. 46, another example valve flap 1234 is shown. The valve flap 1234 includes opposing first and second primary surfaces 1220, 1222, and a stiffening member 1216 extending from the first primary surface 1220. The stiffening member 1216 extends around a peripheral edge of the valve flap 1234. In one arrangement, the stiffening member 1216 extends around an entire peripheral edge or circumference, whereas in other arrangements the stiffening member extends only partially around a peripheral edge of the valve flap. In further arrangements, the stiffening member covers substantially an entire radially outward facing surface of the valve flap that is positioned at a periphery of the valve flap.

The stiffening member 1216 can comprise a different material than the remaining portions of the valve flap 1234. Alternatively, the stiffening member 1216 can comprise the same material, and can be formed concurrently with formation of the remaining portions of the valve flap.

The valve flap 1234 can alternatively be described as having a recess 1224 defined therein. Portions of the valve flap 1234 can have a greater thickness than other portions of the valve flap. The increased thickness portions of the valve flap 1234 provide increased resistance to bending and other bending-related characteristics for the valve flap 1234, and can be considered a stiffening feature of the valve flap.

Figure 47:
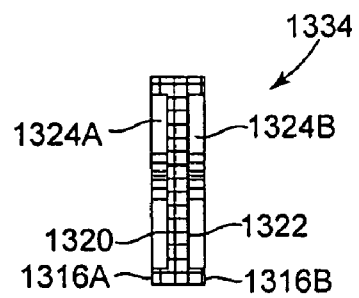

FIG. 47 illustrates a further valve flap configuration 1334 that comprises stiffening members 1316A, 1316B that extend in opposite directions from the first and second primary surfaces 1320, 1322. The valve flap 1334 has recesses 1324A, 1324B defined therein. In other arrangements, such as some of those described below, either one or both of the recesses 1324A, 1324B can be at least partially filled with another material such as, for example, a membrane that at least partially fills at least one of the recesses 1324a, 1324B.

The valve flap 1334 can comprise two separate layers wherein each layer has a construction such as, for example, the construction of valve flap 1234 shown in FIG. 46. The two layers can be separately formed and later secured to each other. Alternatively, the valve flap 1334 can be formed as a single piece.

Some alternative valve flap configurations 1434, 1534, 1634, 1734, 1834, 1934 are illustrated with reference to FIGS. 48-53. The valve flap 1434 shown in FIG. 48 includes two recesses 1424A, 1424B that are arranged on opposing sides of the valve flap. The recesses 1424A, 1424B have a concave shape. Many other shapes for recesses 1424A, 1424B and combinations of shapes are possible. The valve flap 1434 is shown having a greatest material thickness around the peripheral edge thereof. In other arrangements, different portions of the valve flap 1434 besides the peripheral edge can have the greater thickness.

Valve flap 1534 shown in FIG. 49 includes a stiffening member 1516 that extends around a peripheral edge thereof. The stiffening member 1516 has a circular cross-sectional shape that can be described as a bead-type structure. Alternatively, the stiffening member 1516 can be described as two arc-shaped structures that extend from opposing primary surfaces of the valve flap 1534.

FIG. 50 illustrates a valve flap 1634 that has first and second stiffening members 1616A, 1616B of different shapes. The stiffening member 1616A has a generally rectangular cross-section while the stiffening member 1616B has a generally arc-shaped cross-section. Providing different sized and shaped stiffening member structures on opposite sides or at different locations on a valve flap can influence the bending properties of a valve flap.

FIG. 51 illustrates a valve flap 1734 that includes an insert stiffening member 1730 positioned within a recess 1724 defined in the valve flap 1734. The recess 1724 can be defined by a stiffening member 1716 that extends from a primary surface of the valve flap. The insert 1730 can be sized and constructed to at least partially fill the recess 1724. In some arrangements, the member 1730 can extend out of the recess 1724.

A yet further valve flap configuration 1834 is shown in FIG. 52. The valve flap 1834 includes first and second layers 1812, 1814. The first layer 1812 includes a stiffening member 1816 extending from a primary surface 1820. The second layer 1814 can be secured to an opposing side of the first layer 1812 from the stiffening member 1816. A second layer 1814 can possess various characteristics that influence the bending properties of the valve flap 1834.

FIG. 53 illustrates a valve flap 1934 that includes first and second stiffening members 1916A, 1916B. The valve flap 1934 can be formed as an integral unit. In the illustrated embodiment, the stiffening member 1916A, 1916B each have a generally rectangular-shaped construction. The stiffening members 1916A, 1916B can alternatively be defined as a single stiffening member having a greater thickness than the remaining portions of the valve flap 1934. The single stiffening member can define at least in part a peripheral edge of the valve flap 1934.

FIGS. 54-56 illustrate a valve flap 2034 that includes different shaped and sized stiffening members 2016A, 2016B. The stiffening member 2016A extends around a periphery of the valve flap 2034 while the stiffening members 2016B are positioned on a primary surface 2020 radially inward from the stiffening member 2016A. The stiffening member 2016A has a generally rectangular cross-sectional shape as shown in FIGS. 55 and 56. The stiffening member 2016B has a generally arc shaped construction. The size, shape and orientation of the stiffening members 2016A-B can be altered to customize bending characteristics of the valve flap 2034.

FIG. 55 illustrates a valve flap 2034 having a mirror image set of stiffening members 2016C, 2016D extending from an opposing primary surface 2022. The stiffening members 2016C, 2016D can have different shapes and sizes as compared to the stiffening members 2016A, 2016B, and can be positioned at different locations so as not to be mirror images of the stiffening members 2016A, 2016B.

Another valve flap configuration 2134 is shown with reference to FIGS. 57-59. The valve flap 2134 includes a first stiffening member 2116A positioned at a periphery of the valve flap 2134, and a second stiffening member 2116B that is positioned radially inward from the stiffening member 2116A. The stiffening member 2116b can comprise a plurality of linear members that intersect each other. An additional set of stiffening members 2116C, 2116D can extend from an opposite primary surface 2122 from the stiffening members 2116A, 2116B. In some arrangements, the stiffening member 2116B can extend radially outward into engagement with the stiffening member 2116A. Various other shapes, sizes, and numbers of stiffening members can be positioned on the valve flap positioned radially inward from the stiffening member 2116A that is positioned around a periphery of the valve flap 2134.

Figure 60:
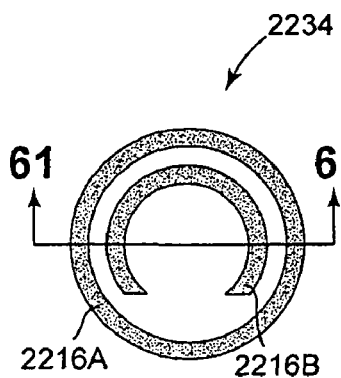
FIG. 60 is a schematic front view of another example valve flap configuration having a plurality of concentric stiffening members, one of which is a partial circumferential construction.
Figure 61:
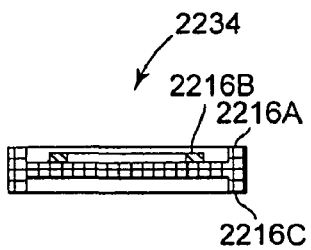
FIGS. 61-62 are schematic cross-sectional side views of the valve flap shown in FIG. 60.
Figure 62:
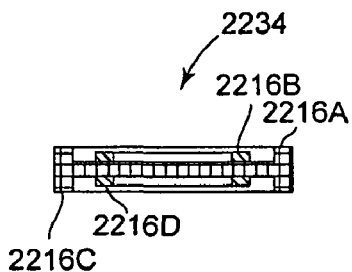

FIGS. 60-68 illustrate still further valve flap configurations that each includes multiple stiffening members. FIGS. 60-62 illustrate a valve flap 2234 that includes a first stiffening member 2216A positioned around a periphery thereof and a second stiffening member 2216B positioned concentric and radially inward from the first stiffening member 2116A. Each of the stiffening members 2216A-B has a generally rectangular cross-sectional area as shown in FIGS. 61 and 62, but can have different cross-sectional shapes and sizes in other arrangements.

The second stiffening member 2216B extends only partially circumferentially. It is possible in other arrangements to provide gaps in the stiffening member so that the stiffening member is not continuous.

The valve flap 2234 can include additional stiffening members 2216C and 2216D on an opposing side of the valve flap for the stiffening members 2216A-B (see FIG. 62). The stiffening members 2216C, 2216D can have different shapes and sizes as well as orientations relative to the stiffening members 2216A-B.

Figure 63:
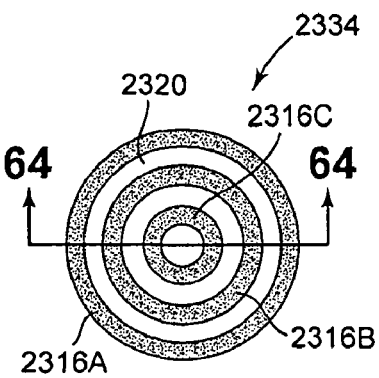
FIG. 63 is a schematic front view of another example valve flap configuration having a plurality of concentric stiffening members.
Figure 64:
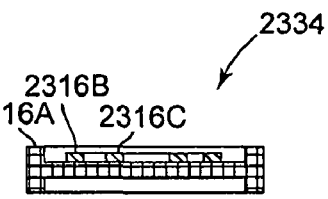
FIGS. 64-65 are schematic cross-sectional side views of the valve flap shown in FIG. 63.
Figure 65:
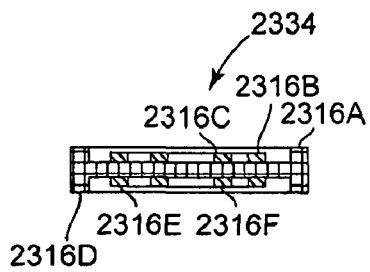

FIGS. 63-65 illustrate a valve flap 2334 that include three concentric circular shaped stiffening members 2316A-C extending from a first primary surface 2320. The stiffening members 2316B-C can have a different shape and size than the stiffening member 2316A (see FIG. 64).

The valve flap 2334 can further comprise an additional set of stiffening members 2316D-F positioned on opposing side of the valve flap from the stiffening members 2316A-C.

Figure 66:
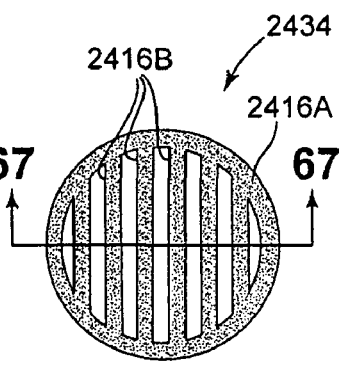
FIG. 66 is a schematic front view of another example valve flap configuration having a plurality of parallel stiffening members.
Figure 67:
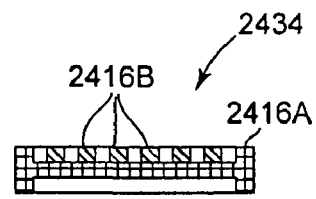
FIGS. 67-68 are schematic cross-sectional side views of the valve flap shown in FIG. 66.
Figure 68:
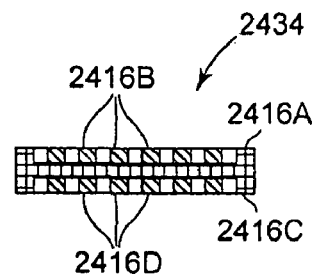

FIGS. 66-68 illustrate a valve flap 2434 that includes a peripherally arranged stiffening member 2416A and a plurality of cross stiffening members 2416B. The cross stiffening members 2416b have a generally linear shape and extend from one portion of the first stiffening member 2416A to another side thereof. The valve flap 2434 can comprise an additional set of stiffening members 2416c and 2416d on an opposing side from the stiffening members 2416A-B.

The stiffening members 2416B are illustrated as being parallel, equally spaced apart, having the same width, and extending into engagement with the stiffening member 2416A. In other arrangements, the stiffening members 2416B can have different shapes, sizes, spacings and orientations relative to each other and to the first stiffening member 2416A as compared to those illustrated in FIGS. 66-68.

Any of the features of any of the valve flap configurations described with reference to FIGS. 44-68 can be combined with or replaced by any other feature described herein.

Further Backflow Prevention Assemblies of FIGS. 69-79

FIGS. 69-79 illustrate some example backflow prevention assemblies that include features that accommodate at least some of the valve flap configurations disclosed above with reference to FIGS. 44-68. FIG. 69 illustrates a backflow prevention assembly 1200 that includes proximal and distal portions 1230, 1232 and the valve flap 1234 shown in FIG. 46. The proximal portion 1230 includes a proximal stiffening member recess 1241. The distal portion 1232 includes a valve seat 56. The proximal stiffening member recess 1241 is sized to receive a portion of the stiffening member 1216 of the valve flap 1234. The recess 1241 can help retain the valve flap 1234 in a fixed radial and axial position relative to the proximal and distal portions 1230, 1234.

FIG. 70 illustrates a backflow prevention assembly 1300 that includes proximal and distal portions 1330, 1332 and a valve flap 1934 (see FIG. 53). The proximal portion 1330 includes a proximal stiffening member recess 1341. The distal portion 1332 defines a valve seat 56 and includes a distal stiffening member recess 1343. The valve flap 1934 includes first and second stiffening members 1916A, 1916b that extend in opposite directions from opposing primary surfaces of the valve flap 1934. The proximal stiffening member recess 1341 is sized to receive a portion of the first stiffening member 1916A. The distal stiffening member recess 1343 is sized to receive a portion of the second stiffening member 1916B. When assembled, the valve flap 1934 is at least partially retained within the recesses 1341, 1343 to help retain the valve flap 1934 in a fixed axial and radial position relative to the proximal and distal portions 1330, 1332.

Another backflow prevention assembly 1400 is illustrated in FIGS. 71-73. The assembly 1400 includes proximal and distal portions 1430, 1432, and a valve flap 1934. The proximal portion 1430 includes at least one biasing protrusion 1438 that biases the valve flap 1934 into a closed position at specific locations on one side of the valve flap 1934. The distal portion 1432 defines a valve seat 56 and includes a retention protrusion 1439. The protrusion 1439 is arranged to engage at least a portion of the valve flap 1934 to support a portion of the valve flap such as, for example, along a center line of the valve flap in alignment with the biasing protrusions 1438.

A backflow prevention assembly 1500 is described with reference to FIG. 74. The assembly 1500 includes proximal and distal portions 1530, 1532 and a valve flap 1234. The proximal portion 1530 includes a biasing protrusion 1538. The distal portion defines a valve seat 56 and includes a retention protrusion 1539. The biasing protrusion 1538 and retention protrusion 1539 are sized and shaped to mate with each other with the valve flap 1234 captured there between. The inner face of the protrusions 1538, 1539 force the valve flap 1234 into a closed orientation. By moving of the valve flap 1234 in a direction opposite the open orientation in combination with the use of a stiffening member 1216 the incidence of the valve flap unintentionally moving into the open state to create flutter and other undesirable effects can be reduced.

FIGS. 75-77 illustrate some alternative constructions for biasing protrusions and proximal stiffening member recesses in the proximal member of a backflow prevention assembly such as the assembly 1300 described above. FIG. 75 illustrates a biasing protrusion 1638 of a proximal portion 1630 that has a generally rectangular cross-section. The proximal stiffening member recess 1641 has a generally rectangular cross-sectional shape and is positioned directly adjacent the protrusion 1638.

FIG. 76 illustrates a proximal portion 1730 that includes a biasing protrusion 1738 having a pointed construction such as a triangular cross-section. A pointed recess 1741 is positioned adjacent to the protrusion 1738. The recess 41 is defined in part by the shape of the protrusion 1738.

FIG. 77 illustrates a portion of a proximal portion 1830 that includes a biasing protrusion 1838 and a proximal stiffening member recess 1841. The protrusion 1838 includes a tapered portion with a truncated end. Many other shapes and sizes for the protrusion 1838 are possible. Likewise, the shape, size and relative position of the recess 41 compared to the protrusion 1838 is possible in other arrangements.

FIGS. 78-79 illustrate a proximal housing portion 1930 and a distal housing portion 1932. The proximal portion 1930 includes a proximal stiffening member recess 1941 and a biasing protrusion 1938. The distal portion 1932 includes a distal stiffening member recess 1943, a biasing protrusion 1939, and sealing edges 1947a, 1947b along the valve seat 56. The recesses 1941, 1943 have a size and shape that permits some movement of portions of a valve flap (e.g., stiffening members 1916a, 1916b as shown in FIG. 79) relative to the housing portions 1930, 1932 when the valve flap is in various positions, such as a closed position against the valve seat 56. The shape and size of the recesses 1941, 1943 and the protrusions 1916a, 1916b can promote contact of the valve flap at one or more sealing edge (e.g., point 1947b show in FIG. 79) when the valve flap is retained between the housing portions 1920, 1932.

Any of the backflow prevention assemblies and in particular the proximal portion thereof can include the features of FIGS. 69-79 and other features to accommodate various valve flap configurations.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment. Therefore, the spirit and scope of the appended claims should not be limited to the description of the preferred versions contained herein.

The claimed invention is:

1. A vacuum backflow prevention system, comprising:
   a fluid ejector tube adapted for insertion into a patient's mouth;
   a backflow prevention device, comprising:
      a distal portion defining a valve seat portion and an inlet, the distal portion operably connected to the fluid ejector tube;
      a proximal portion defining an outlet, the proximal portion configured for operative connection to the distal portion;
      a valve member retained between the proximal and distal portions at a single location along a peripheral edge of the valve member, the valve member being moveable from a first position substantially blocking fluid flow between the inlet and the outlet, and a second position wherein at least a portion of the valve member is moved in a direction toward the outlet to permit fluid to flow from the inlet to the outlet under a vacuum condition, the valve member having a stiffening structure extending from a surface of the valve member that faces the outlet on a portion of the valve member that is moved toward the outlet in the second position, the stiffening structure providing increased resistance to movement of the at least a portion of the valve flap from the first position to the second position;
      wherein the stiffening structure extends around a circumference of the valve member to provide an increased thickness of the valve member around the circumference.

2. The system of claim 1, wherein the stiffening structure is a second layer of material positioned on the valve member.

3. The system of claim 1, wherein the stiffening member provides a variable thickness in the valve member.

4. The system of claim 1, wherein the valve member includes at least first and second stiffening structures.

5. The system of claim 1, wherein the stiffening structure has a shape selected from the group consisting of hemispherical, linear, and circular.

6. The system of claim 1, wherein the stiffening structure defines a rim feature that extends from opposing primary surfaces of the valve member.

7. The system of claim 1, wherein at least one of the proximal and distal portions includes a recessed portion sized to receive a portion of the stiffening structure.

8. The system of claim 1, wherein the distal portion includes a valve seat against which a portion of the valve member engages in the first position to block fluid flow, and a stiffening structure recess defined in the valve seat, the stiffening structure recess being sized to receive a portion of the stiffening structure when the valve member is in the first position.

9. A backflow prevention device, comprising:
   a distal portion defining a distal opening;
   a proximal portion defining a proximal opening; and
   a valve member positioned at a location between the distal portion and the proximal portion along only a portion of a peripheral edge of the valve member, the valve member being automatically moveable from a first position substantially blocking fluid flow between the distal opening and the proximal opening, and a second position wherein a portion of the valve member is moved toward the proximal opening to permit fluid to flow between the distal opening and the proximal opening upon application of a predetermined fluid force to the valve member, the valve member including a stiffening structure extending in a proximal direction from a primary surface of the valve member that faces the proximal opening and extending around a perimeter of the valve member, the stiffening structure being positioned on the portion of the valve member that moves toward the proximal opening, the stiffening structure providing a variable thickness in the valve member.

10. The device of claim 9, wherein the predetermined fluid force is a vacuum force applied at the proximal opening.

11. The device of claim 9, wherein the stiffening structure is a second layer of material positioned on the valve member.

12. The device of claim 9, wherein the valve member includes at least first and second stiffening structures.

13. The device of claim 9, wherein the stiffening structure has a shape selected from the group consisting of hemispherical, linear, and circular.

14. The device of claim 9, wherein the stiffening structure defines a rim feature that extends from opposing primary surfaces of the valve member.

15. The device of claim 9, wherein at least one of the proximal and distal portions includes a recessed portion sized to receive a portion of the stiffening structure.

16. The device of claim 9, wherein the distal portion includes a valve seat against which a portion of the valve member engages in the first position to block fluid flow, and a stiffening structure recess defined in the valve seat, the stiffening structure recess being sized to receive a portion of the stiffening structure when the valve member is in the first position.

17. The device of claim 9, wherein the stiffening structure provides an increased thickness of the valve member around the periphery.

18. A vacuum backflow prevention system, comprising:
   a fluid ejector tube adapted for insertion into a patient's mouth;
   a backflow prevention device, comprising:
   a distal portion defining a valve seat portion and an inlet, the distal portion operably connected to the fluid ejector tube;
   a proximal portion defining an outlet, the proximal portion configured for operative connection to the distal portion;
   a valve member retained between the proximal and distal portions at a single location along a peripheral edge of the valve member, the valve member being moveable from a first position substantially blocking fluid flow between the inlet and the outlet, and a second position wherein at least a portion of the valve member is moved in a direction toward the outlet to permit fluid to flow from the inlet to the outlet under a vacuum condition, the valve member having a stiffening structure extending from a surface of the valve member that faces the outlet on a portion of the valve member that is moved toward the outlet in the second position, the stiffening structure providing increased resistance to movement of the at least a portion of the valve flap from the first position to the second position;
   wherein the stiffening structure defines a rim feature that extends from opposing primary surfaces of the valve member.

19. The system of claim 18, wherein the stiffening structure is a second layer of material positioned on the valve member.

20. The system of claim 18, wherein the stiffening member provides a variable thickness in the valve member.

21. The system of claim 18, wherein the stiffening structure extends around a circumference of the valve member to provide an increased thickness of the valve member around the circumference.

22. The system of claim 18, wherein the valve member includes at least first and second stiffening structures.

23. The system of claim 18, wherein the stiffening structure has a shape selected from the group consisting of hemispherical, linear, and circular.

24. The system of claim 18, wherein the stiffening structure defines a rim feature that extends from opposing primary surfaces of the valve member.

25. The system of claim 18, wherein at least one of the proximal and distal portions includes a recessed portion sized to receive a portion of the stiffening structure.

26. The system of claim 18, wherein the distal portion includes a valve seat against which a portion of the valve member engages in the first position to block fluid flow, and a stiffening structure recess defined in the valve seat, the stiffening structure recess being sized to receive a portion of the stiffening structure when the valve member is in the first position.

* * * * *

UNITED STATES PATENT AND TRADEMARK OFFICE
CERTIFICATE OF CORRECTION

PATENT NO.         : 8,256,464 B2                                       Page 1 of 1
APPLICATION NO.    : 12/163377
DATED              : September 4, 2012
INVENTOR(S)        : Richard Paul Bushman and Jerry Schueller It is certified that error appears in the above-identified patent and that said Letters Patent is hereby corrected as shown below:

Cover Page, Related U.S. Application Data, Item 63:

Line 1, change "Continuation" to --Continuation-in-part--

Line 2, change "continuation" to --continuation-in-part--

Signed and Sealed this
Twenty-third Day of October, 2012

David J. Kappos
*Director of the United States Patent and Trademark Office*